US006194158B1

(12) United States Patent
Kroes et al.

(10) Patent No.: US 6,194,158 B1
(45) Date of Patent: Feb. 27, 2001

(54) DIAGNOSTIC ASSAY FOR CANCER

(75) Inventors: Roger A. Kroes, Lake Zurich; Joseph R. Moskal, Chicago; Hirotaka Yamamoto, Glenview, all of IL (US)

(73) Assignee: NYXIS NeuroTherapies, Inc., Chicago, IL (US)

( * ) Notice: Subject to any disclaimer, the term of this patent is extended or adjusted under 35 U.S.C. 154(b) by 0 days.

(21) Appl. No.: 09/438,938

(22) Filed: Nov. 12, 1999

Related U.S. Application Data

(60) Provisional application No. 60/108,120, filed on Nov. 12, 1998, and provisional application No. 60/145,640, filed on Jul. 27, 1999.

(51) Int. Cl.[7] ............... C12Q 1/68; C12P 19/34; C07H 21/02; C07H 21/04
(52) U.S. Cl. ............ 435/6; 435/91.2; 435/91.4; 536/22.1; 536/23.1
(58) Field of Search ............ 435/6, 91.2, 91.4; 536/22.1, 23.1

(56) References Cited

U.S. PATENT DOCUMENTS

| | | | |
|---|---|---|---|
| 4,683,195 | 7/1987 | Mullis et al. | 435/6 |
| 5,104,792 | 4/1992 | Silver et al. | 435/6 |
| 5,262,311 | 11/1993 | Pardee et al. | 435/91.2 |
| 5,426,039 | 6/1995 | Wallace et al. | 435/91.2 |
| 5,459,037 | 10/1995 | Sutcliffe et al. | 435/6 |
| 5,556,752 | 9/1996 | Lockhart et al. | 435/6 |
| 5,578,832 | 11/1996 | Trulson et al. | 250/458.1 |
| 5,580,726 | 12/1996 | Villeponteau et al. | 435/6 |
| 5,593,839 | 1/1997 | Hubbell et al. | 435/6 |
| 5,599,672 | 2/1997 | Liang et al. | 435/6 |
| 5,599,695 | 2/1997 | Pease et al. | 435/91.1 |
| 5,599,696 | 2/1997 | Mueller et al. | 435/91.2 |
| 5,631,734 | 5/1997 | Stern et al. | 356/317 |
| 5,665,547 | 9/1997 | Pardee et al. | 435/6 |
| 5,688,648 | 11/1997 | Mathies et al. | 435/6 |
| 5,700,644 | 12/1997 | Gould et al. | 435/6 |
| 5,710,000 | 1/1998 | Sapolsky et al. | 435/6 |
| 5,712,126 | 1/1998 | Weissman et al. | 435/91.2 |
| 5,733,729 | 3/1998 | Lipshutz et al. | 435/6 |
| 5,744,300 | 4/1998 | Linskens et al. | 435/6 |
| 5,744,305 | 4/1998 | Fodor et al. | 435/6 |
| 5,744,306 | 4/1998 | Murtagh, Jr. et al. | 435/6 |
| 5,753,439 | 5/1998 | Smith et al. | 435/6 |
| 5,753,788 | 5/1998 | Fodor et al. | 536/22.1 |
| 5,759,776 | 6/1998 | Smith et al. | 435/6 |
| 5,770,456 | 6/1998 | Holmes | 436/518 |
| 5,770,722 | 6/1998 | Lockhart et al. | 536/25.3 |
| 5,776,683 | 7/1998 | Smith et al. | 435/6 |
| 5,801,001 | 9/1998 | Sager et al. | 435/7.23 |
| 5,807,680 | 9/1998 | Sutcliffe et al. | 435/6 |
| 5,814,445 | 9/1998 | Belyavsky et al. | 435/6 |
| 5,861,293 | 1/1999 | Kojiri et al. | 435/193 |
| 5,922,601 | 7/1999 | Baetscher et al. | 435/456 |
| 5,965,409 | 10/1999 | Pardee et al. | 435/91.2 |
| 5,968,784 | 10/1999 | Spinella et al. | 435/91.1 |
| 5,994,076 | 11/1999 | Chenchik et al. | 435/6 |

OTHER PUBLICATIONS

Der, et al., (1998), *Proc. Natl. Acad. Sci. USA*, vol. 95, pp. 15623–15628.
Gray, et al., (1998), *Science*, vol. 281, pp. 533–537.
Harkin, et al., (1999), *Cell*, vol. 97, pp. 575–586.
Lockhart, et al., (1969), *Nature Biotechnology*, vol. 14, p. 1675–1680.
Meuillet et al., (1999), *Cancer Research*, vol. 59, pp. 234–240.
Petretti, et al., (1999), *Biochimica et Biophysica Acta*, 1428:209–218.
Wang, et al., (1999), *FEBS Letters*, 445:269–273.
Alwine, et al., (1977), *Proc. Natl. Acad. Sci.USA*, 74:5350–5354.
Melton, et al., (1984), *Nuc. Acids Res.*, 12:7035.
Berchtold, (1989), *Nuc. Acids Res.*, 17(1):453.
Mok et al., (1994), *Gynecologic Oncology*, 52:247–252.
Liang and Pardee, (1992), *Science*, 257:967–971.
Liang, et al., (1993), *Nucleic Acids Research*, 21(14):3269–3275.
Wang, et al., (1996), *Trends in Pharmacological Science*, 17(8):276–279.
Uchiyama, et al., (1995), *Neurosurgery*, 37(3):464–469.
Sehgal, et al., (1997), *J. of Surgical Oncology*, 64:102–108.
Sehgal, et al., (1997), *Int. J. Cancer*, 71:565–572.
Shinoura, et al., (1995), *Cancer Letters*, 89:215–221.
Kito, et al., (1997), *Gene*, 184:73–81.
Schena, et al., *Proc. Natl. Acad. Sci. USA*, Oct. 1, 1996; 93(20):10614–10619.
Heller, et al., *Proc. Natl. Acad. Sci. USA*, Mar. 18, 1997; 94(6):2150–2155.
Engels et al., *Angew. Chem. Int. Ed. Engl.*, 28:716–734 (1989).
Szer, et al., *J. Rheumatol.*, (1994) Nov.; 21(11):2136–2142.
Wichmann, et al., *Hum. Immunol.*, 1999; Jan. 60(1):57–62.
Sierakowska, et al., *Clin. Exp Immunol*, 1993; Dec. 94(3):435–439.
Murray, et al., *J. Rheumatol.*, 1997; Mar. 24(3):560–567.
Dong, et al., *Arthritis Rheum*, 1998; Aug. 41(8):1505–1510.
Arnaudo, et al., *J. Rheumatol.*, 1998; Sep. 25(9):1861–1862.
Patel, et al., (1994), *Human Gene Therapy*, 5:577–584.
*Human Gene Therapy*, Apr. 1994, vol. 5, pp. 543–563.
Stratford–Perricaudet, L., and M. Perricaudet, (1991), in *Human Gene Transfer*, O. Cohen–Haguenauer and M. Boiron, eds., Editions John Libbey Eurotect, France, vol. 219, pp. 51–61.

(List continued on next page.)

Primary Examiner—Jeffrey Fredman
Assistant Examiner—Amun Kr. Chakrabarti
(74) Attorney, Agent, or Firm—McDonnell, Boehnen, Hulbert & Berghoff

(57) ABSTRACT

The invention is directed towards gene expression characteristic for cancer, in particular brain cancers such as glioblastoma. Compositions, methods and kits encompassing such therein.

18 Claims, 5 Drawing Sheets

OTHER PUBLICATIONS

Levrero, et al., (1991), *Gene*, 101:195–202.
Graham and Prevec, (1992), in *Vaccines: New Approaches to Immunological Problems*, R.W. Ellis, ed., Butterworth–Heinemann, Boston, pp. 363–390.
Stratford–Perricaudet, et al., (1992), *J. Clin. Invest.*, 90:626–630.
Rich, et al., (1993), *Human Gene Ther.*, 4:461–476.
Crystal, et al., (1994), *Nature Genetics*, 8:42–51.
Rosenfeld, et al., (1992), *Cell*, 68:143–155.
Quantin, et al., (1992), *Proc. Natl. Acad. Sci. USA*, 89:2581–2584.
Herz and Gerard, (1993), *Proc. Natl. Acad. Sci. USA*, 90:2812–2816.
Le Gal La Salle, et al., (1993), *Science*, 259:988–990.
Hermonat and Muzyczka, (1984), *Proc. Natl. Acad. Sci. USA*, 81:6466–6470.
Geller and Federoff, (1991), in *Human Gene Transfer*, O. Cohen–Haguenauer and M. Borion, eds., Editions John Libbey Eurotext, France, vol. 219, pp. 63–73.
Glorioso, et al., (1995), in *Viral Vectors—Gene Therapy and Neuroscience Application*, M.G. Kaplitt and A.D. Loewy, eds., Academic Press, New York, pp. 1–23.
Smith and Moss, (1983), *Gene*, 25:21–28.
Moss, (1992), *Semin. Virol.*, 3:277–283.
Miller and Rosman, (1989), *BioTechniques*, 7(9):980–990.
Oldfield, et al., (1993), *Human Gene Therapy*, 4:36–69.
Mulligan, (1993), *Science*, 260:926–932.
Doll, et al., (1996), *Gene Therapy*, 3:437–447.
Badie, et al. (1994), *Neurosurgery*, 35(5):910–916.
Perez–Cruet, et al., (1994), *J. Neur. Res.*, 39:506–511.
Chen, et al., (1994), *Proc. Natl. Acad. Sci USA*, 91:3054–3057.
Culver, et al., (1994), *Human Gene Therapy* 5:343–379.
Yamamoto, et al., (1997), *Brain Research*, 755(1):175–179.
Eguchi, et al., (1991), *Annu. Rev. Biochem.*, 67:631–652.
Verma & Eckstein, (1998), *Annu. Rev. Biochem.*, 67:99–134.

FIGURE 1

```
   1 GAATTCGCGG CCGCGTCGAC GCGGGCACTC AAAATCTTGG TAAGGAAAGT CCCATTTGGG
  61 CAAAAATATG TCGCTGACTA CGCAGGTAAT AAGGTTAGGC TCAGAGGTAT CCATGGGAAC
 121 CACTAATAAA AGTACTAGAA TATGTTTGGG AAGGAAATAT TGGAAACGGG TGAAAACTTA
 181 CTGAGGGACA CATGCAATGG TACTAAATCA TCACATACAG CACTATCATT AAAATGTAAT
 241 TAGATTAGTG GAGGAACCCA TCTACCATAT TTACAATCCC ATATAATCAT TACACAATAA
 301 TCACATAATC ATATTAATGC TATGGAGTAT GTATTTATCC TCATTTTACA TGTGAAGCGG
 361 CGGCAGCTGC TTGGGCGCGG TGCGGTGGTG ACTGAGCTAC GAGCCTGGCG GCGGGTGTGC
 421 GCCGAGCCCC GGCCCGGCCC GGCCCTCGCG TGCCTCCCAG GCTCCGCACC CCTGATGCTG
 481 CGCGGGTGCT GAGCCCGCTT CGGCCGGGAC GATGGTGAAG TATTTCCTGG GCCAGAGCGT
 541 GCTCCGGAGT TCCTGGGACC AAGTGTTCGC CGCCTTCTGG CAGCGGTACC CGAATCCCTA
 601 TAGCAAACAT GTCTTGACGG AAGACATAGT ACACCGGGAG GTGACCCCTG ACCCGGAACT
 661 GCTGTCCCGG CGACTCCTGA CCAAGACCAA CAGGATGCCA CGCTGGGCCG AGCGACTATT
 721 TCCTGCCAAT GTTGCTCACT CGGTGTACGT CCTGGAGGAC TCTATTGTGG ACCCACAGAA
 781 TCAGACCATG ACTACCTTCA CCTGGAACAT CAACCACGCC CGGCTGATGG TGGTGGAGGA
 841 ACGATGTGTT TACTGTGTGA ACTCTGACAA CAGTGGCTGG ACTGAAATCC GCCGGGAAGC
 901 CTGGGTCTCC TYTAKCTTAT TTGGKGTCTC CAGAGCTGTC CAGGAATTTG GTCTTGCCCG
 961 GTTCAAAAGC AACGTGACCA AGACTATGAA GGGTTTTGAA TATATCTTGG CTAAGCTGCA
1021 AGGCGAGGCC CCTTCCAAAA CACTTGTTGA CACAGCCAAG GAAGCCAAGG AGAAGGCAAA
1081 GGAGACGGCA CTGGCAGCTA CAGAGAAGGC CAAGGACCTC GCCAGCAAGG CGGCCACCAA
1141 GAAGCAGCAG CAGCAGCAAC AGTTTGTGTA GCCAGTCTAC CACCACCACA GCACCCCAGA
1201 CAGCTAGGCT TAGCCCCTCT GCCCTCCCTT CATTGTACTT TATCATTAAA AATCAACTTC
1261 CAGCCCTGTT TGCTGTTTAC GTGGTGGGTT GTGGGGATGC AGTTGGCAT TTGCAGTACA
1321 CCAAGCACAT GATTCATGTT TGAGCCAGGT CTGCTTATTC TCCCATTGGG CAGCTGAGGA
1381 CCGAGGCACA GAGGTGCGGT GACTTGCCCG GGGCTTCAGG TAGCCTGCAG GTTAACTGGC
1441 GGTAAGTGCT AGACTGTAAG CCCGACAAGG GCAGGGCTTT TGGTTTTGTT CTCTGATGTG
1501 TCTCAGTATT TAGCACATAA TAGACACTCA ATAAATACTT GTTGAATTC   (SEQ ID NO.: 8)
```

FIGURE 2

```
1    GAATTCGCGG CCGCGTCGAC CAAGGAAGAG TCTTCAGATG ATGAAGATAA AGAAAGTGAA
61   GAGGAGCCAC CAAAAAAGAC AGCCAAAAGA GAAAAACCTA AACAGAAAGC TACTTCTAAA
121  AGTAAAAAAT CTGTGAAAAG TGCCAATGTT AAGAAAGCAG ATAGCAGCAC CACCAAGAAG
181  AATCAAAACA GTTCCAAAAA AGAAAGTGAG TCTGAGGATA GTTCAGATGA TGAACCTTTA
241  ATTAAAAAGT TGAAGAAACC CCCTACAGAT GAAGAGTTAA AGGAAACAAT AAAGAAATTA
301  CTGGCCAGTG CTAACTTGGA AGAAGTCACA ATGAAACAGA TTTCGCAAAA AGGTCTATGA
361  AAATTATCCT ACTTATGATT TAACTGAAAG AAAAGATTTC ATAAAAACAA CTGTAAAAGA
421  GCTAATTTCT TGAGATAGAG GACAGAGAAG ATGACTCGTT CCCATAGATT GAAGATCTG
481  ATTTATACCA TTATACCAGC AAAGAGAATG TATTTCCTTT TCTAAATCCT TGTTAAGCAA
541  CGTTAGTAGA ACTTACTGCT GACCTTTTA TCTTGAGTGT TATGTGAATT TGAGTTTGCT
601  GTTTTAAATT GCATTCTAT GCCATTTTA GTTTAAAATC TTGCATGGCA TTAATTGTTC
661  CTTGCTTTTA TAGTTGTATT TTGTACATTT TGGATTTCTT TATATAAGGT CATAGATTCT
721  TGAGCTGTTG TGGTTTTTAG TGCACTTAAT ATTAGCTTGC TTAAGGCATA CTTTTAATCA
781  AGTAGAACAA AAACTATTAT CACCAGGATT TATACATACA GAGATTGTAG TATTTAGTAT
841  ATGAAATATT TTGAATACAC ATCTCTGTCA GTGTGAAAAT TCAGCGGCAG TGTGTCCATC
901  ATATTAAAAA TATACAAGCT ACAGTTGTCC AGATCACTGA ATTGGAACTT TTCTCCTGCA
961  TGTGTATATA TGTCAAATTG TCAGCATGAC AAAAGTGACA GATGTTATTT TTGTATTTTT
1021 AAAAAACAAT TGGTTGTATA TAAAGTTTTT TTATTTCTTT TGTGCAGATC ACTTTTTAAA
1081 CTCACATAGG TAGGTATCTT TATAGTTGTA GACTATGGAA TGTCAGTGTT CAGCCAAACA
1141 GTATGATGGA ACAGTGAAAG TCAATTCAGT GATGGCAACA CTGAAGGAAC AGTTACCCTG
1201 CTTTGCCTCG AAAGTGTCAT CAATTTGTAA ATTTAGTATT AACTCTGTAA AAGTGTCTGT
1261 AGGACGTTTT ATATTATATA AGGCAGNCCN AAAATCAACC TATCAAAGCT TCAAAAACTT
1321 TGGGAAAGGG TGGGATTAAG CCAAGCACAT TTGGCTTACA GTAAATGAAC TGATTTTTAT
1381 TAACTGCTTT TGCCCATATA AATGCTGAT ATTTACTGGA AACCTAGCCA GCTTCACGAT
1441 TATGNCTAAA GTNCCNGATT ATAATGCCAG AATATAATGT GCAGGCAATC GTGGATGTCT
1501 CTGACAAAGT GTGTCTCAAA AATAATATNC TTTTACATTA AGAAATTTA ATGTTTCTCT
1561 GGAAAAAAAA AAAAAAAAAA AAAAGTCGAC GCGGCCGCGA ATTC (SEQ ID NO.: 9)
```

DIAGNOSTIC ASSAY FOR CANCER

This application claims is a continuation-in-part of U.S. Provisional Application No. 60/108,120 filed Nov. 12, 1998 and U.S. Provisional Application No. 60/145,640 filed Jul. 27, 1999.

FIELD OF THE INVENTION

The invention relates to the field of brain cancer, in particular characteristic genes and gene expression useful in screening for, diagnosis of, monitoring of, and therapeutic treatment of cancer.

BACKGROUND OF THE INVENTION

Cancer can develop in any tissue of any organ at any age. Most cancers detected at an early stage are potentially curable; thus, physicians need a heightened awareness of predisposing inherited and environmental factors. The ability to screen patients for genetic predisposition for cancer can greatly assist in the monitoring of high-risk patients for early signs of cancer, and thus allowing for early intervention. (See for example, *The Merck Manual of Diagnosis and Therapy*, 16th ed., Merck & Co., (1992)).

Malignant brain tumors (for example glioma, meningiomas, and schwannomas) are common, with an incidence of 4.5 per 100,000. The most common tumor types in adults are gliomas and meningiomas. The most common tumors in children are astrocytomas, medulloblastomas, ependymomas, and brain stem gliomas. In children, brain tumors are one of the most common causes of death from cancer. (See for example, *Professional Guide to Disease*, 3rd ed., Springhouse Corp., (1989)).

Clinically, brain tumors can be characterized by their cell type and location, along with other phenotypic clues. Malignant brain tumors are sometimes catagorized as glioblastoma multiforme (spongioblastoma multiforme), astrocytoma, oligodendroglioma, ependyoma, medulloblastoma, meningioma, schwannoma, and pituitary tumors. It is also possible that cancer originating in other tissues, such as lung, liver, pancreas, colon, prostate etc., can metastasize to the brain, thus forming tumors that are not of brain origin, potentially causing confusion as to the source of cancer.

Cancer is a cellular malignancy whose unique trait—loss of normal control mechanisms—results in unregulated growth, lack of differentiation, and ability to invade local tissues and metastasize. Thus cancer cells are unlike normal cells, and are potentially identifiable by not only their phenotypic traits, but also by their biochemical and molecular biological characteristics. In particular, the altered phenotype of cancer cells indicates altered gene activity, either unusual gene expression, or gene regulation. Identification of gene expression products or proteins associated with cancer cells will allow for the molecular characterization of malignancies. The ability to specifically characterize suspected cancers, and to potentially identifiy not only cell type, but also predisposition for metastasis and any sensitivity to particular anti-cancer thereapy, is most useful for determining not only the course of treatment, but also the likelihood of success.

Thus, the discovery of specific, brain tumor characteristic gene expression is a useful and important tool useful in screening for, diagnosis of, monitoring of, and therapeutic treatment of brain cancer.

SUMMARY OF THE INVENTION

The identification of characteristic, nucleic acid signals is a useful and important discovery which allows for compositions, assays, kits and reagents suitable for the characterization of various brain cancers. Provided herein are reagents and methods for ascertaining the propensity of a cell for malignant phenotype said cell being isolated or in a biological sample, said method comprising assaying a cell or biological sample to be tested for a signal indicating the transcription of a nucleic acid transcript. In a preferred embodiment, the nucleic acids are substantially identical to the sequences of Table I, SEQ ID NOS. 1–9, and known as CINN 1, CINN 2, OP2 C2-6, OP7 C3-1, OP9 A4-2, OP11 C1-3, OP11 G2-10, FAS OP13 C1-D, FAS OP17 C1-D, dek, laminin α-chain gene, α-NAC gene, ribosomal protein L35a, and ribosomal protein L7a. Also provided are methods for monitoring cancer progession or the effectiveness of a treatment regimen, and methods for identifying compounds that affect expression of genes involved in cancer.

BRIEF DESCRIPTION OF THE FIGURES

The invention in all of its several aspects, can be better understood by reference to the following figures, wherein:

FIG. 1 depicts the nucleic acid sequence of the insert from clone CINN-1,

FIG. 2 depicts the nucleic acid sequence of the insert from clone CINN-2.

Figure 3:
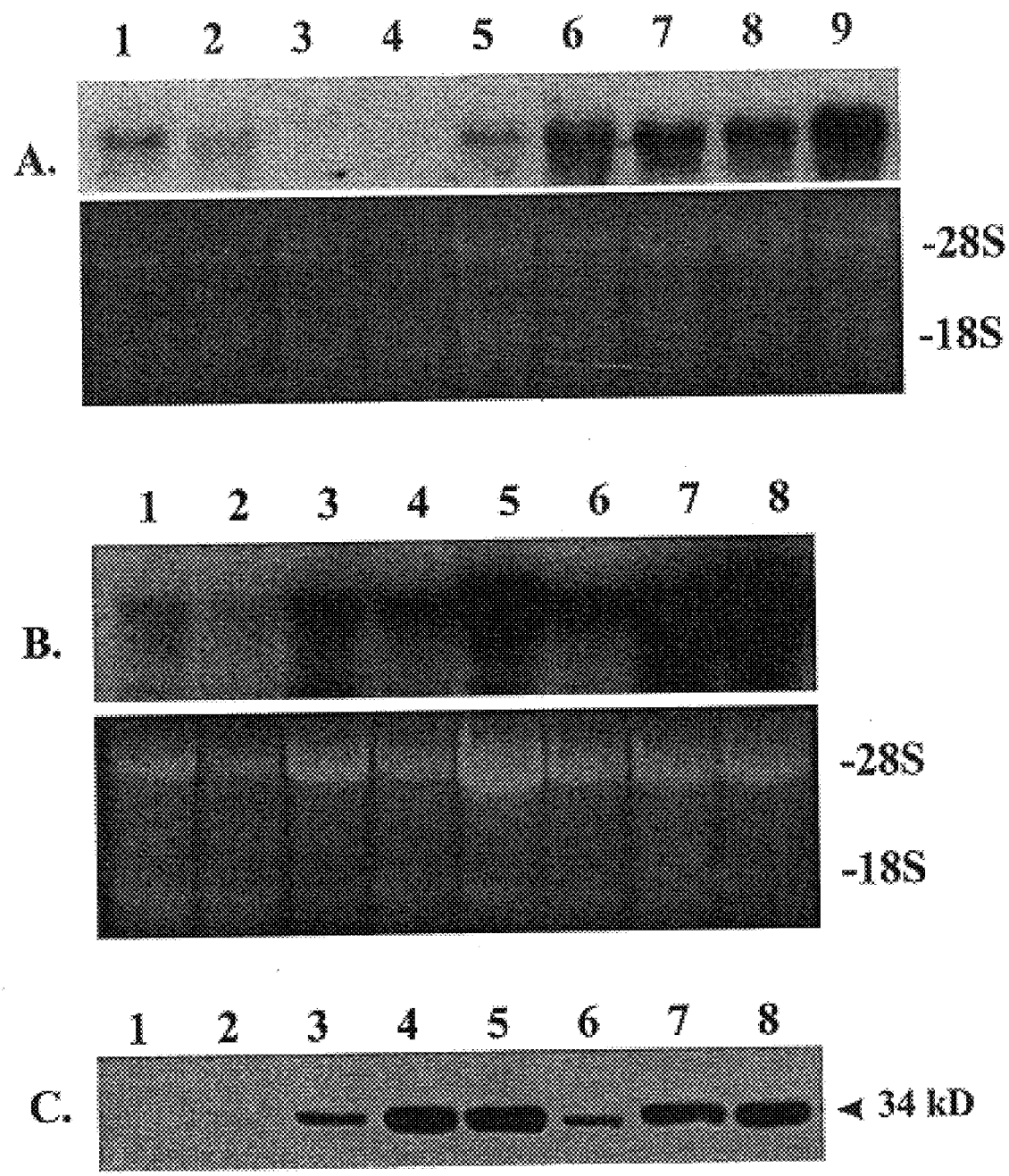
FIG. 3 depicts the expression of dek in glioma specimens and human glioma cell lines. A. 25 μg of total RNA per lane were used for Northern analysis. Upper panel: lanes 1–2: normal human brain, lane 3: Grade I glioma, lane 4: Grade II glioma, lanes 5–6: Grade III gliomas, lanes 7–9: Grade IV gliomas (glioblastoma). Ethidium bromide staining of total RNA (Lower panel). B. 25 μg of total RNA per lane were used for Northern analysis. Upper panel: lane 1–2: normal human brain, lanes 3–8: human glioma cell lines, U373MG, U87MG, U118MG, D54, SW1088, and SNB19, respectively. Ethidium bromide staining of total RNA (Lower panel). C. Western blot analysis of dek protein expression. 20 μg of whole cell lysate protein from each cell line was separated on discontinuous SDS/PAGE, transferred to a nylon membrane and probed with an anti-dek monoclonal antibody, as described. Specific signal was detected with horseradish peroxidase-conjugated secondary antibody and ECL detection. Lane 1–2, normal brain; Lanes 3–8, U373MG, U87MG, U118MG, D54, SW1088, and SNB19, respectively. The arrowhead indicates the 43 kDa immunoreactive dek product.

μg of cell lysate protein from cells transfected with each of the chimeric CAT constructs were incubated at 37° C. for 20 hours in the presence of 40 μM [$^3$H]chloramphenicol and 240 μM n-butyryl Coenzyme A. The reaction products were extracted with xylene and n-butyrylated chloramphenicol determined by liquid scintillation counting.

One of ordinary skill in the art will be able to understand and ascertain modifications and embodiments of the present invention that fall within the spirit and scope of the disclosure as described below.

DETAILED DESCRIPTION OF THE INVENTION

It is believed that brain tumorigenesis results from complex interactions of multiple and cumulative genetic alterations. These events lead to either the activation of various oncogenes, overriding regulatory signals which control cell proliferation, or inactivation of tumor suppressor genes, resulting in the uncontrolled growth of cells. (See for example Burck et al., *Oncogenes*, Springer-Verlag, New York, 1988). The identification and characterization of subsets of the genes associated with such uncontrolled growth is essential in order to understand the process of malignancy, but more importantly, useful for the identification of specific cancerous tissues, and tissues that are premalignant, and potentially predisposed for it.

Cancer is defined herein as any cellular malignancy for which a loss of normal cellular controls results in unregulated growth, lack of differentiation, and increased ability to invade local tissues and metastasize. Cancer may develop in any tissue of any organ at any age. Cancer may be an inherited disorder or caused by environmental factors or infectious agents; it may also result from a combination of these.

The differential expression of genes that regulate cell growth, migration, and other functions enables a cell to grow out of control and become cancerous. In many cases, the activation of oncogenes, which override the intrinsic cellular growth regulatory commands of a cell, as well as the inactivation of tumor suppressor genes, which normally hold tumor formation in check, renders tumor cells free of growth restraints. The identification and characterization of these differentially expressed genes in malignant tumors will facilitate the understanding of the basic nature of the malignancy and yield novel molecular markers useful in diagnosis and treatment. For the purposes of utilizing the present invention, the term cancer includes both neoplasms and premalignant cells.

In one embodiment, the present invention is useful for the diagnosis and treatment of many types of cancers including, for example, cancers of the breast, prostate, colon, and lung. In a preferred embodiment, the reagents and methodologies provided herein are useful for the diagnosis and treatment of brain cancer. Brain tumors (or brain cancer) arise as a result of complex interactions of multiple and cumulative genetic alterations. Brain cancer is defined herein as any cancer involving a cell of neural origin. Examples of brain cancers include but are not limited to intracranial neoplasms such as those of the skull (i.e., osteoma, hemangioma, granuloma, xanthoma, osteitis deformans), the meninges (i.e., meningioma, sarcoma, gliomatosis), the cranial nerves (i.e., glioma of the optic nerve, schwannoma), the neuroglia (i.e., gliomas) and ependyma (i.e., ependymomas), the pituitary or pineal body (i.e., pituitary adenoma, pinealoma), and those of congenital origin (i.e., craniopharygioma, chordoma, germinoma, teratoma, dermoid cyst, angioma, hemangioblastoma) as well as those of metastatic origin.

As demonstrated herein, it has been discovered that brain cancer cells, in particular glioma cells, express certain nucleic acid sequences at a higher level than that found in normal brain cells, for example fetal astrocytes. Similarly, it has been found that this expression is most commonly detected as a nucleic acid, usually mRNA which is expressed from an activated gene, resulting in a detectable nucleic acid signal corresponding to the transcript from a gene. The present invention teaches a specific array of gene signals, i.e. expressed genes, mRNA transcripts, which indicate a cells propensity for a malignant phenotype in cancer. In a preferred embodiment, the gene sequences provided herein are indicative of brain cancer. In addition, the present invention provides an assay system for the detection of cancer and the monitoring of treatment progress. The present invention further provides novel nucleic acid sequences representing genes and the polypeptides encoded thereby that are involved in cancer progression.

I. General Methodology

Within this application, unless otherwise stated, the techniques utilized may be found in any of several well-known references including: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), Berger et al., *Guide to Molecular Cloning Techniques, Methods in Enzymology*, Vol. 152, Academic Press, Inc., (1987); Davis et al., *Basic Methods in Molecular Biology*, Elsevier Science Publishing Co., Inc. (1986); Ausubel et al., *Short Protocols in Molecular Biology*, 2nd ed., John Wiley & Sons, (1992), Grinsted et al., *Plasmid Technology, Methods in Microbiology*, Vol. 21, Academic Press, Inc., (1988); Symonds et al., *Phage Mu*, Cold Spring Harbor Laboratory Press (1987), Guthrie et al., *Guide to Yeast Genetics and Molecular Biology, Methods in Enzymology*, Vol. 194, Academic Press, Inc., (1991), *PCR Protocols: A Guide to Methods and Applications* (Innis, et al. 1990. Academic Press, San Diego, Calif.), McPherson et al., *PCR Volume 1*, Oxford University Press, (1991), *Culture of Animal Cells: A Manual of Basic Technique, 2$^{nd}$ Ed.* (R. I. Freshney. 1987. Liss, Inc. New York, N.Y.), and *Gene Transfer and Expression Protocols*, pp. 109–128, ed. E. J. Murray, The Humana Press Inc., Clifton, N.J.). The basic principles of eukaryotic gene structure and expression are generally known in the art. (See for example Hawkins, *Gene Structure and Expression*, Cambridge University Press, Cambridge, UK, 1985; Alberts et al., *The Molecular Biology of the Cell*, Garland Press, New York, 1983; Goeddel, *Gene Expression Technology, Methods in Enzymology*, Vol. 185, Academic Press, Inc., (1991); Lewin, *Genes VI*, Oxford Press, Oxford, UK, 1998). Each of the above-mentioned references and any of those listed below including issued patents are hereby incorporated by reference.

For the purposes of this application, a transcriptional regulatory region is defined as any region of a gene involved in regulating transcription of a gene, including but not limited to promoters, enhancers and repressors. A transcriptional regulatory element is defined as any element involved in regulating transcription of a gene, including but not limited to promoters, enhancers and repressors. A promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation by the nucleic acid of amino acids, start and stop signals in a three base "triplet" code. Promoters are often upstream ("5' to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. The term operably linked refers to the combination of a first nucleic acid fragment representing a transcriptional control region having activity in a cell joined to a second nucleic acid fragment encoding a reporter or effector gene such that expression of said reporter or effector gene is influenced by the presence of said transcriptional control region.

A responsive element is a portion of a transcriptional control region that induces expression of a nucleotide sequence following the interaction of a cell with a compound. There may be multiple responsive elements within a single transcriptional control region and each of these elements may function independently of any other elements of that transcriptional control region. Thus, a responsive element may be incorporated into a reporter gene vector independent from the remainder of the transcriptional control region from which it is derived and function to drive expression of the reporter gene under the proper conditions.

The terms overexpressed or underexpressed typically relate to expression of a nucleic acid sequence or protein in a tumor cell at a higher or lower level, respectively, than that level typically observed in a non-tumor cell (ie, normal control). In certain cases, the terms overexpressed or underexpressed may also relate to the expression level in a cell that has been contacted by a compound as compared to the expression level in a similar cell that has not been contacted by the compound.

The terms cancer cell and tumor cell may be used interchangeably and relate to cells found within a cancerous growth or tumor. The reagents and methodologies provided herein are applicable to the detection, diagnosis, and treatment of many types of cancers. In a preferred embodiment, the reagents and methodologies provided herein are useful for the detection, diagnosis, and treatment of brain cancer.

For the purposes of this application, hybridization is typically performed under stringent conditions. The term "stringent conditions" refers to hybridization and washing under conditions that permit only binding of a nucleic acid molecule such as an oligonucleotide or cDNA molecule probe to highly homologous sequences. For example, a stringent wash solution is 0.015 M NaCl, 0.005 M NaCitrate, and 0.1% SDS used at a temperature of 55° C.–65° C. Another stringent wash solution is 0.2× SSC and 0.1% SDS used at a temperature of between 50° C.–65° C.

A DNA or amino acid sequence is identical to another sequence where the sequences are identical. A DNA or amino acid sequence is substantially identical or substantially the same as another sequence where the sequences are 50–100% identical. In a preferred embodiment, substantially identical sequences share 60–100% identity, more preferably 70–100% identity, even more preferably 80–100% identity and even more preferably 90–100% identity. In a most preferred embodiment, substantially identical sequences share 95–100% identity.

The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', $F(ab')_2$ and F(v).

A polypeptide refers to an amino acid sequence encoded by a nucleic acid, a fragment thereof, or a nucleic acid comprising a nucleic acid of this invention. Preferably, the nucleic acids of this invention are those described by Table I and SEQ ID Nos. 1–9.

The word inoculum in its various grammatical forms is used herein to describe a composition containing a polypeptide of this invention as an active ingredient used for the preparation of antibodies against the polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term polypeptide and its various grammatical forms.

II. Detection of Nucleic Acids

In one embodiment, the present invention provides for the detection of gene expression where said detected signal is detected as a polynucleotide (such as an RNA, mRNA, DNA, cDNA, or other nucleic acid) or a protein/polypeptide. It should be understood by the skilled artisan that many methods for detection of such signals exist and that any suitable method for detection is encompassed by the instant invention. Typical assay formats utilizing nucleic acid hybridization includes, and are not limited to, 1) nuclear run-on assay, 2) slot blot assay, 3) northern blot assay (Alwine, et al. Proc. Natl. Acad. Sci. 74:5350), 4) magnetic particle separation, 5) Nucleic Acid or DNA chips, 6) reverse northern blot assay, 7) dot blot assay, 8) in situ hybridization, 9) RNase protection assay (Melton, et al. Nuc. Acids Res. 12:7035 and as described in the 1998 catalog of Ambion, Inc., Austin, Tex.), 10) ligase chain reaction, 11) polymerase chain reaction (PCR), 12) reverse transcriptase (RT)-PCR (Berchtold, et al. Nuc. Acids. Res. 17:453), and, 13) differential display RT-PCR (DDRT-PCR) or other suitable combination of techniques and assays. Methods for detection which can be employed include, and are not limited to 1) radioactive labels, 2) enzyme labels, 3) chemiluminescent labels, 4) fluroescent labels, or other suitable labels. Such methodologies and labels are well known in the art and widely available to the skilled artisan.

In an exemplary embodiment, the RNase protection assay may be utilized in the present invention by hybridizing multiple DNA probes corresponding to a one or more members of a panel of sequences to mRNA isolated from a tumor cell and performing the RNase assay. An increase or a decrease in the expression of the sequences from the tumor cell as compared to normal cells indicates that the genes related to those sequences may be involved in tumorigenesis. In a preferred embodiment, the panel is selected from the sequences of Table I or SEQ ID NOS. 1–9.

In another embodiment, multiple DNA probes capable of hybridizing to mRNA corresponding to a reporter sequence under the transcriptional control of a nucleic acid sequence overexpressed in tumor cells transcriptional control region may be utilized. Exemplary reporter sequences may include β-galactosidase, luciferase, CAT, and green fluorescent protein. An increase or a decrease in the expression of the sequences from the tumor cell as compared to normal cells indicates that the genes related to those sequences may be involved in tumorigenesis. In a preferred embodiment, the panel is selected from the sequences of Table I or SEQ ID NOS. 1–9.

The screening assays of the present invention are also well suited for polymerase chain reaction (PCR) amplification, whether the format of such assays are in solution after isolation of mRNA and subsequent direct amplification or such after reverse transcription. Such assays can be performed on isolated biological samples or extracted fluids, using a suitable PCR assay format. The screening methods and compositions of the present invention are also amendable to routine adaptation to automated screening systems employing computer controlled reagent aliquoting and signal detection.

With a known gene target, it is possible to apply standard PCR to assay tissue for specific gene expression (Mok et al., (1994), *Gynecologic Oncology,* 52: 247–252). However, detection of unknown gene expression requires additional manipulations before a useful gene can be identified. Differential Display Reverse Transcriptase Polymerase Chain Reaction (DDRT-PCR) is a powerful tool useful for isolating large numbers of expressed nucleic acids, corresponding to gene expression. Several U.S. Patents have been issued relating to methods in this and related methods, including U.S. Pat. Nos. 5,599,672, 5,807,680, 5,459,037, 5,814,445, 5,104,792, 4,683,195, 5,665,547, 5,262,311, 5,599,696, and 5,712,126, to name a few (all of which are hereby incorporated by reference in their entirety). DDRT-PCR has been described by Liang and Pardee (1992), *Science,* 257: 967–971; Liang et al., (1993), *Nucleic Acids Research,* 21(14): 3269–3275; and Wang et al., (1996), *Trends in Pharmacological Science,* 17(8): 276–9.

Previous attempts to assay brain tumors include the studies of Uchiyama et al., (1995), *Neurosurgery,* 37(3): 464–469; Sehgal et al., (1997), *J. of Surgical Oncology,* 64: 102–108; Sehgal et al., (1997), *Int. J. Cancer,* 71: 565–572; Shinoura et al., (1995), *Cancer Letters,* 89: 215–221; and Kito et al., (1997), *Gene,* 184: 73–81. However, the direct application of DDRT-PCR to brain tumor samples results in a large number of signals corresponding to expressed genes, not all of which are useful for characterizing the cancerous nature of the brain tumor. Selection of the most significant signals from the large number of signals initially generated, and the assembly of a panel of characeristic nucleic acid targets requires insightful consideration and comparison of the data, followed by re-analysis and assessment of the correctness of such choices. The instant invention provides such a method for the identification of over- or underexpressed sequences in cancer. Preferably, the cancer is of neural origin.

Once identified, the specific nucleic acid targets identified as being characteristic for brain cancer can be readily adapted to automated detection assays for use in diagnosis or screening of patients for predisposition for brain cancer. Modification of the discovery of the unique panel of signals of the present invention for use in such screening or diagnostic assays would be well within the skill of one of ordinary art, and require only routine experimentation. In another embodiment, detection of a nucleic acid such as an mRNA may be accomplished using a gene chip. For instance, the sequences of interest maybe arrayed upon a chip as described in any of the available gene chip technologies such as that described by Schena, et al. (*Parallel human genome analysis: microarray-based expression monitoring of* 1000 *genes.* Proc Natl Acad Sci USA Oct. 1, 1996;93(20):10614–9). In that study, DNA "chips" were used to quantitatively monitor differential expression of heat shock and phorbol ester-regulated genes in human T cells. Heller, et al. (*Discovery and analysis of inflammatory disease-related genes using cDNA microarrays.* Proc Natl Acad Sci USA March 18, 1997; 94(6):2150–5) used DNA chips to profile expression of selected human genes of probable significance in inflammation as well as with genes expressed in peripheral human blood cells. In that study, mRNA from cultured macrophages, chondrocyte cell lines, primary chondrocytes, and synoviocytes provided expression profiles for selected cytokines, chemokines, DNA binding proteins, and matrix-degrading metalloproteinases. From the peripheral blood library, tissue inhibitor of metalloproteinase 1, ferritin light chain, and manganese superoxide dismutase genes were identified as expressed differentially in rheumatoid arthritis compared with inflammatory bowel disease. Several other methods for utilizing DNA chips are known, including the methods described in U.S. Pat. Nos. 5,744,305; 5,733,729; 5,710,000; 5,631,734; 5,599,695; 5,593,839; 5,578,832; 5,556,752; 5,770,722; 5,770,456; 5,753,788; 5,688,648; 5,753,439; 5,744,306 (all of which are incorporated by reference in their entirety).

Adaptation of the teachings of the present invention for nucleic acid or gene chip technology as described above would be routine, following the methods and teachings known in the art. The instant invention provides a DNA chip comprising specific sequences for measuring expression levels of certain sequences within a cancer cell to determine whether expression is up- or down-regulated. For instance, a DNA chip comprising nucleotide sequences capable of hybridizing to one or more members of a panel of DNA sequences may be synthesized using commonly available techniques. mRNA is isolated from a normal, non-cancer cell and a cancer cell and hybridized to the DNA chip comprising one of more of the sequences from the panel. Hybridization is then detected by any of the available methods. In such a manner, sequences that are either overexpressed or underexpressed in a cancer cell as compared to a normal cell are. In a similar manner, mRNA from a cancer cell that has been contacted with a compound may be hybridized to sequences on the DNA chip to determine whether that compound affects expression of a particular sequence. The appropriate controls should be included such that a true comparison can be made. In a preferred embodiment, the panel is selected from the sequences shown in Table I or SEQ ID NOS. 1–9.

The invention provides for a kit comprising hybridization probes specific for at least two nucleic acid sequences selected from the group consisting of the characteristic nucleic acid sequences that are over- or under-expressed in a cancer cell. Preferably, the sequences are substantially identical to those identified in Table I or SEQ ID NOS. 1–9. In a preferred embodiment, the invention encompasses screening assays for the detection of the expression of at least one of the characteristic nucleic acid sequences identified in Table I or SEQ ID NOS. 1–9 below for the diagnosis of potentially cancerous tissues or cells. The invention provides for such a kit, further comprising suitable reaction buffer components. The invention also provides for such a kit wherein said probes are suitable for use in PCR amplification of the specific target, direct or indirect hybridization assay, RNase protection assay. In particular, such screening assays can be performed on tissue biopsy samples, serum samples, cerebro-spinal fluid samples, or any other suitable biological sample.

In another embodiment of the invention, genomic screening assays are contemplated for the detection of specific single nucleotide polymorphisms (SNP) in a nucleic acid sequence found to be over- or under-expressed in a cancer cell. Preferably, the sequence is substantially identical to those listed in Table I or SEQ ID NOS. 1–9. In a preferred embodiment, such genomic screening is used to detect any predisposition for cancer formation, as an aid to assist monitoring for potential cancer episodes in the future.

Screening assays for detection of at least one of nucleic acids found to be over- or under-expressed in a cancer cell can be designed on the basis of specific hybridization, under stringent conditions, of at least one probe encompassing a specific nucleic acid sequence. Preferably, the sequence is substantially identical to those of Table I or SEQ ID NOS. 1–9 below, fragment of such nucleic acid sequence, or as the assay format may require, the complementary nucleic acid sequence, or fragment thereof. The assay can be designed to detect a single species of nucleic acid that is substantially identical to the sequences of Table I or SEQ ID NOS. 1–9 in a single assay, or using the properly distinqishable signal mechanisms, more than one specific species per reaction.

In particular, the present invention teaches that the presence of detectable nucleic acid signal corresponding to the nucleic acid sequence of the cDNAs (described more fully below) named CINN 1, CINN 2, OP2 C2-6, OP7 C3-1, OP9 A4-2, OP11 C1-3, OP11 G2-10, FAS OP13 C1-D, and FAS OP17 C1-D is characteristic of brain cancer, and in particular glioma. Thus it is a further aspect of the present invention that the detection of nucleic acid corresponding to novel human genes containing the nucleic acid sequence of CINN 1, OP11 C1-3, FAS OP13 C1-D, or FAS OP17 C1-D is indicative of cancer potential. It is a further aspect of the present invention that detection of a nucleic acid signal having a nucleic acid squence corresponding to at least a portion of human dek, laminin α-chain gene, α-NAC gene, ribosomal protein L35a, or ribosomal protein L7a is also indicative of cancer potential. Thus the present invention encompasses the detection of nucleic acid corresponding to four (4) novel genes, and five (5) other human genes, as being characteristic of brain cancer, glioma in particular. The present invention also encompasses detection of less than the complete panel of nine (9) characteristic signals as being an indicator of potential or early cancer.

III. Methods for Cloning

The identification and isolation of the full-length genes associated with the nucleic acids that found to be over- or under-expressed in a cancer cell will allow for the generation of recombinant proteins, via recombinant DNA methodologies, which can be used in numerous ways to prepare and screen for therapeutics that will interact with the protein, such as antibodies and chemical agents. Preferably, the sequence is substantially identical to a sequence of Table I or SEQ ID NOS. 1–9.

A full length polypeptide or fragment thereof encoded by a nucleic acid of the instant invention can be prepared using well known recombinant DNA technology methods such as those set forth in Sambrook et al. (Molecular Cloning: A Laboratory Manual, Cold Spring Harbor Laboratory Press, Cold Spring Harbor, N.Y. [1989]) and/or Ausubel et al., eds, (Current Protocols in Molecular Biology, Green Publishers Inc. and Wiley and Sons, N.Y. [1994]). A gene or cDNA encoding protein or fragment thereof may be obtained for example by screening a genomic or cDNA library, or by PCR amplification. Improved methods of cloning in vitro amplified nucleic acids are described in Wallace et al., U.S. Pat. No. 5,426,039.

For screening, the probe preferably has a nucleotide sequence corresponding to, complementary to, or substantially identical to a sequence over- or under-expressed in a cancer cell, preferably being a sequences substantially identical to a sequence of Table I or SEQ ID NOS. 1–9, or a fragment thereof. To probe a cDNA or genomic library using an oligonucleotide probe, the following exemplary hybridization conditions may be utilized: 6×.SSC with 0.05 percent sodium pyrophosphate at a temperature of 35° C.–62° C., depending on the length of the oligonucleotide probe. For example, 14 base pair probes may be washed at 35–40° C., 17 base pair probes may be washed at 45–50° C., 20 base pair probes may be washed at 52–57° C., and 23 base pair probes may be washed at 57–63° C. The temperature can be increased 2–3° C. where the background non-specific binding appears high. Another exemplary protocol uses tetramethylammonium chloride (TMAC) for the washing step. An exemplary stringent washing solution is 3 M TMAC, 50 mM Tris-HCl, pH 8.0, and 0.2% SDS. As described above, the washing temperature using this solution is a function of the length of the probe (ie, a 17 base pair probe is washed at about 45–50° C.).

Alternatively, a gene encoding the polypeptide or fragment may be prepared by chemical synthesis using methods well known to the skilled artisan such as those described by Engels et al. (Angew. Chem. Intl. Ed., 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the polypeptide will be several hundred nucleotides in length. Nucleic acids larger than about 100 nucleotides can be synthesized as several fragments using these methods. The fragments can then be ligated together to form the full length polypeptide. Usually, the DNA fragment encoding the amino terminus of the polypeptide will have an ATG, which encodes a methionine residue. This methionine may or may not be present on the mature form of the polypeptide, depending on whether the polypeptide produced in the host cell is secreted from that cell.

The gene or cDNA so isolated can be inserted into an appropriate expression vector for expression in a host cell. The vector is typically selected to be functional in the particular host cell employed (i.e., the vector is compatible with the host cell machinery such that amplification of the gene and/or expression of the gene can occur). The polypeptide or fragment thereof may be amplified/expressed in prokaryotic, yeast, insect (baculovirus systems) and/or eukaryotic host cells. Selection of the host cell will depend at least in part on whether the polypeptide or fragment thereof is to be glycosylated and/or phosphorylated. If so, yeast, insect, or mammalian host cells are preferable; yeast cells can typically glycosylate and phosphorylate the polypeptide, and insect and mammalian cells can glycosylate and/or phosphorylate the polypeptide as it naturally occurs on the TRIP1 polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element.

IV. Methods for Detection of Polypeptides

The invention provides for a method wherein a protein encoded by said expressed gene is detected by protein gel assay, antibody binding assay, or other such detection as is known in the art. For instance, the present invention contemplates a kit comprising specific probes for detection of a polypeptide product (or fragment thereof) of a sequence that is over- or underexpressed in a cancer cell where such probe can be functionalized antibody protein, polyclonal antibody, monoclonal antibody, or antigen binding fragment of such proteins. Preferably, the nucleic acid encoding the polypeptide or fragment thereof is substantially identical to a sequence of Table I or SEQ ID NOS. 1–9.

An antibody of the present invention, in one embodiment, is characterized as comprising antibody molecules that immunoreact with a protein encoded by a nucleic acid over- or under-expressed in cancer. Preferably, the nucleic acid is substantially identical to a sequence of Table I or SEQ ID NOS. 1–9. Preferably, an antibody further immunoreacts with the protein in situ, i.e., in a tissue section. Thus, the invention describes an anti-protein antibody that immunoreacts with any of the polypeptides of this invention, preferably also immunoreacts with the recombinant protein corresponding to a nucleic acid of the instant invention, and more preferably also reacts with a native protein in situ in a tissue section.

An antibody of the present invention is typically produced by immunizing a mammal with an inoculum containing a polypeptide of this invention and thereby induce in the mammal antibody molecules having immunospecificity for immunizing polypeptide. The antibody molecules are then collected from the mammal and isolated to the extent desired by well known techniques such as, for example, by using DEAE Sephadex or Protein G to obtain the IgG fraction.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v). Fab and F(ab')$_2$ portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The preparation of antibodies against polypeptide is well known in the art. See Staudt et al., *J. Exp. Med.*, 157:687–704 (1983), or the teachings of Sutcliffe, J. G., as described in U.S. Pat. No. 4,900,811, the teaching of which are hereby incorporated by reference. Briefly, to produce a peptide antibody composition of this invention, a laboratory mammal is inoculated with an immunologically effective amount of a polypeptide of this invention typically as present in a vaccine of the present invention. The anti-polypeptide antibody molecules thereby induced are then collected from the mammal and those immunospecific for both a polypeptide and the corresponding recombinant protein are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

For a polypeptide that contains fewer than about 35 amino acid residues, it is preferable to use the peptide bound to a carrier for the purpose of inducing the production of antibodies. One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, U.S. Pat. No. 3,791,932 and U.S. Pat. No. 3,839,153. In addition, a site-directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958. Exemplary additional linking procedures include the use of Michael addition reaction products, di-aldehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like. The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms ($\mu$g) to about 500 milligrams (mg) per inoculation (dose), preferably about 50 micrograms to about 50 milligrams per dose. The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition. Inocula can also include an adjuvant as part of the diluent. Adjuvants such as complete Freund's adjuvant (CFA), incomplete Freund's adjuvant (IFA) and alum are materials well known in the art, and are available commercially from several sources.

The antibody so produced can be used, inter alia, in the diagnostic methods and systems of the present invention to detect a polypeptide of the present invention in a sample such as a tissue section or body fluid sample. Anti-polypeptide antibodies that inhibit function of the polypeptide can also be used in vivo in therapeutic methods as described herein. A preferred anti-polypeptide antibody is a monoclonal antibody. The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. A preferred monoclonal antibody of this invention comprises antibody molecules that immunoreact with a polypeptide of the present invention. More preferably, the monoclonal antibody also immunoreacts with recombinantly produced whole protein.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature*, 256:495–497 (1975), the description of which is incorporated by reference. The hybridoma supernates so prepared can be screened for the presence of antibody molecules that immunoreact with a polypeptide.

Briefly, to form the hybridoma from which the monoclonal antibody composition is produced, a myeloma or other self-perpetuating cell line is fused with lymphocytes obtained from the spleen of a mammal hyperimmunized with a antigen, such as is present in a polypeptide of this invention. The polypeptide-induced hybridoma technology is described by Niman et al., *Proc. Natl. Acad. Sci., USA*, 80:4949–4953 (1983), the description of which is incorporated herein by reference. It is preferred that the myeloma cell line used to prepare a hybridoma be from the same species as the lymphocytes. Typically, a mouse of the strain 129 GlX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively. Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques. Media useful for the preparation of these compositions are both well known in the art and commercially available and include synthetic culture media, inbred mice and the like. An exemplary synthetic medium is Dulbecco's Minimal Essential Medium (DMEM; Dulbecco et al., *Virol.* 8:396 (1959)) supplemented with 4.5 gm/l glucose, 20 mM glutamine, and 20% fetal calf serum. An exemplary inbred mouse strain is the Balb/c. Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1989).

The monoclonal antibodies of this invention can be used in the same manner as disclosed herein for antibodies of the present invention. For example, the monoclonal antibody can be used in the therapeutic, diagnostic or in vitro methods disclosed herein where immunoreaction with [gene product] is desired. Also contemplated by this invention is the hybridoma cell, and cultures containing a hybridoma cell that produce a monoclonal antibody of this invention.

It is also possible to isolated antibodies reactive against polypeptides of the instant invention using phage display techniques. Display of antibody fragments on the surface of viruses which infect bacteria (bacteriophage or phage) makes it possible to produce human sFvs with a wide range of affinities and kinetic characteristics. To display antibody fragments on the surface of phage (phage display), an antibody fragment gene is inserted into the gene encoding a phage surface protein (pIII) and the antibody fragment-pIII fusion protein is expressed on the phage surface (McCafferty et al. (1990) Nature, 348: 552–554; Hoogenboom et al. (1991) Nucleic Acids Res., 19: 4133–4137). For example, a sFv gene coding for the V.sub.H and V.sub.L domains of an anti-lysozyme antibody (D1.3) was inserted into the phage gene III resulting in the production of phage with the DI.3 sFv joined to the N-terminus of pIII thereby producing a "fusion" phage capable of binding lysozyme (McCafferty et al (1990) Nature, 348: 552–554). The skilled artisan may also refer to Clackson et al. (1991) Nature, 352: 624–628), (Marks et al. (1992) Bio/Technology, 10: 779–783), Marks et al Bio/Technology, 10: 779–785 (1992) for further guidance. In the instant case, the antibody fragment gene is isolated from the immunized mammal, and inserted into the phage display system. Phage containing antibodies reactive to the polypeptide are then isolated and characterized using well-known techniques. Kits and services are available for generating antibodies by phage display from well-known sources such as Cambridge Antibody Technology Group plc (United Kingdom).

Autoantibodies to the polypeptides of the instant invention may also be detected using techniques well-known and widely available to the skilled artisan. For detection of autoantibodies in the serum of a patient by an antigen-antibody reaction, various conventional immunologically methods can be used such as a method of directly measuring a reaction in a liquid phase and a solid phase and a method of measuring an inhibitory reaction immunologically by adding an inhibiting substance. The following are the examples of the above-mentioned detecting methods, (1) aggregation reaction; (2) DID: double immune diffusion method (Octarony method); (3) ELISA: enzyme linked immunoabsorbent assay, (4) FIA: fluorescent immunosorbent assay, (5) nephlometry method, (6) radioimmuno assay (RIA), (7) immunofluorescent methods. Such methods are described in available references such as U.S. Pat. No. 5,976,810.

The presence of elevated levels of certain nucleic acids or polypeptides, such as dek in gliomas (see below) has potential for development of diagnostic reagents. dek has been shown to be an autoantigen in several diseases, such as juvenile rheumatoid arthritis, lupus erythematosis, and Kikuchi's Disease (Szer et al. *A novel autoantibody to the putative oncoprotein DEK in pauciarticular onset juvenile rheumatoid arthritis.* J Rheumatol 1994 November;21(11) :2136–42; Wichmann et al. *Autoantibodies to transcriptional regulation proteins DEK and ALY in a patient with systemic lupus erythematosus.* Hum Immunol 1999 January;60(1):57–62; Sierakowska et al. *The putative oncoprotein DEK, part of a chimera protein associated with acute myeloid leukaemia, is an autoantigen in juvenile rheumatoid arthritis.* Clin Exp Immunol 1993 December;94 (3):435–9; Murray et al. *Antibodies to the 45 kDa DEK nuclear antigen in pauciarticular onset juvenile rheumatoid arthritis and iridocyclitis: selective association with MHC gene.* J Rheumatol 1997 March;24(3):560–7; Dong et al. *Autoantibodies to DEK oncoprotein in a patient with systemic lupus erythematosus and sarcoidosis.* Arthritis Rheum 1998 August;41(8):1505–10; Amaudo et al. *Antibodies to the DEK protein in Kikuchi's disease.* J Rheumatol 1998 September;25(9):1861–2). The present invention provides for the evaluation of the presence of dek autoantibodies in the serum of glioma patients. The existence of such autoantibodies may provide the foundation for both a novel non-invasive diagnostic for gliomas as well as a method for evaluation of tumor recurrence following treatment.

V. Methods of Treatment a. Pharmacogenomics

The invention further provides for a method of ascertaining propensity for malignancy, monitoring the progress of chemotherapy or other anticancer therapy, screening for re-occurence of cancer, or other similar detection of present or potential cancer, where such method detects for the expression of at least one gene which is over- or under-expressed in a cancer cell. In a preferred embodiment, the gene is nucleic acid sequence sharing substantial identity to a nucleic acid sequence selected from the sequences of Table I or SEQ ID NOS. 1–9. Preferably, the group consists of CINN 1, CINN 2, OP2 C2-6, OP7 C3-1, OP9 A4-2, OP11 C1-3, OP11 G2-10, FAS OP13 C1-D, and FAS OP17 C1-D, human dek gene, laminin α-chain gene, α-NAC gene, ribosomal protein L35a gene, and ribosomal protein L7a gene. The present invention provides for a method for ascertaining the propensity for malignant phenotype of cells in a biological sample, said method comprising assaying a biological sample to be tested for a signal indicating the transcription of a nucleic acid transcript, wherein said transcript is from at least one gene selected from the group consisting essentially of the genes encoded for by or containing the characteristic nucleic acid sequences identified in Table I and SEQ ID Nos. 1–9.

In a further embodiment of the invention, screening assays of biological samples are contemplated, where such assays are conducted during the course of chemotherapy alone, or after surgical intervention to treat cancer, to monitor for the continued presence or return of cancerous cells. Such screening assays are designed to detect for the presence of expressed nucleic acids corresponding to any of those listed in Table I below and SEQ ID Nos. 1–9, as an indicator of the possible tumor recurrence. Such monitoring will quickly identify the effective anti-cancer drugs suitable for treatment of the identified brain cancer. In particular, such methods allow for identifying suitable combination therapies.

Related to the use described above, the methods and compositions of the present invention allow for a therapeutic prediction of the efficacy of any contemplated therapy or therapeutic on the specific brain cancer. By determining the characteristic gene expression features, and testing cells for modulation of such gene expression, it is possible to determine the potential responsiveness of the target brain cancer, to the proposed therapeutic.

Genetic Screening is also made possible, as detecting mutations within the genes indicated by the nucleic acid sequences that are over- or underexpressed in a cancer cell. Preferably, the sequences are those in Table I or SEQ ID NOS. 1–9. Using the sequences or the control elements of such genes, it is possible to detect and identify persons with a potential predisposition for cancer, and thus bring medical monitoring early in the persons life.

In another embodiment, the present invention provides for a method for monitoring the progression of cancer or the effectiveness of a treatment regimen in a patient. Changes in the expression of certain sequences indicates whether or not a treatment regimen is having an effect in the patient. For example, if a certain treatment regimen results in increased expression of a sequence known to be associated with metastasis, it may be an indication that the treatment is not working to the benefit of the patient.

b. Gene Therapy

The present invention further provides for methods of treating a patient by inhibiting or introducing expression into the cells of a patient a nucleic acid or fragment thereof that shows increased or decreased expression in a tumor cell. The use of gene therapy to augment or ameliorate the expression of the genes associated with the nucleic acid sequences that are over- or under-expressed in tumor cells is also contemplated. In particular, the use of antisense molecules to interfere with mRNAs corresponding to the genes identified by such sequences. It is also possible to construct recombinant DNA vectors which can affect targeted homologous recombination to delete or substitute such genes with normal or non-malignant forms. In a preferred embodiment, the sequences are substantially identical to the sequences of Table I or SEQ ID NOS. 1–9.

In practicing the present invention, it is advantageous to transfect into a cell a nucleic acid construct directing expression of a protein or nucleic acid product having the ability to alter the behavior of the cell. There are available to one skilled in the art multiple viral and non-viral methods suitable for introduction of a nucleic acid molecule into a target cell. Genetic manipulation of primary tumor cells has been described previously (Patel et al., 1994. *Human Gene Therapy* 5, p. 577–584). Genetic modification of a cell may be accomplished using one or more techniques well known in the gene therapy field (*Human Gene Therapy* April 1994, Vol. 5, p. 543–563; Mulligan, R. C. 1993). Viral transduction methods may comprise the use of a recombinant DNA or an RNA virus comprising a nucleic acid sequence that drives or inhibits expression of a protein to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes but is not limited to a retrovirus or Sindbis virus. It is to be understood by those skilled in the art that several such DNA and RNA viruses exist that may be suitable for use in the present invention.

Adenoviral vectors have proven especially useful for gene transfer into eukaryotic cells (Stratford-Perricaudet, L., and M. Perricaudet. 1991. *Gene transfer into animals: the promise of adenovirus*. p. 51–61, *In: Human Gene Transfer*, Eds, O. Cohen-Haguenauer and M. Boiron, Editions John Libbey Eurotext, France). Adenoviral vectors have been successfully utilized to study eukaryotic gene expression (Levrero, M., et al. 1991. *Defective and nondefective adenovirus vectors for expressing foreign genes in vitro and in vivo.* Gene 101: 195–202), vaccine development (Graham, F. L., and L. Prevec (1992) *Adenovirus-based expression vectors and recombinant vaccines*. In Vaccines: New Approaches to Immunological Problems, (Ellis, R. V. Ed.), pp. 363–390. Butterworth-heinemann, Boston), and in animal models (Stratford-Perricaudet, et al. 1992. *Widespread long-term gene transfer to mouse skeletal muscles and heart. J. Clin. Invest.* 90, 626–630; Rich, et al. 1993. *Development and analysis of recombinant adenoviruses for gene therapy of cystic fibrosis. Human Gene Ther.* 4, 461–476). The first trial of Ad-mediated gene therapy in human was the transfer of the cystic fibrosis transmembrane conductance regulator (CFTR) gene to lung (Crystal, et al. 1994. *Nature Genetics* 8, 42–51). Experimental routes for administrating recombinant Ad to different tissues in vivo have included intratracheal instillation (Rosenfeld, et al. 1992. *In vivo transfer of the human cystic fibrosis transmembrane conductance regulator gene to the airway epithelium. Cell* 68, 143–155) injection into muscle (Quantin, B., et al. 1992. *Adenovirus as an expression vector in muscle cells in vivo. Proc. Natl. Acad. Sci. USA* 89, 2581–2584), peripheral intravenous injection (Herz, J. and R. D. Gerard. 1993. *Adenovirus-mediated transfer of low density lipoprotein receptor gene acutely accelerates cholesterol clearance in normal mice. Proc. Natl. Acad. Sci. USA* 90, 2812–2816) and stereotactic inoculation to brain (Le Gal La Salle, et al. 1993. *An adenovirus vector for gene transfer into neurons and glia in the brain. Science* 259, 988–990). The adenoviral vector, then, is widely available to one skilled in the art and is suitable for use in the present invention.

Adeno-associated virus (AAV) has recently been introduced as a gene transfer system with potential applications in gene therapy. Wild-type AAV demonstrates high-level infectivity, broad host range and specificity in integrating into the host cell genome (Hermonat, P. L., and N. Muzyczka. 1984. *Use of adeno-associated virus as a mammalian DNA cloning vector: transduction of neomycin resistance into mammalian tissue culture cells. Proc. Natl. Acad. Sci. USA* 81: 6466–6470). Herpes simplex virus type-1 (HSV-1) is attractive as a vector system for use in the nervous system because of its neurotropic property (Geller, A. I., and H. J. Federoff. 1991. *The use of HSV-1 vectors to introduce heterologous genes into neurons: implications for gene therapy. In: Human Gene Transfer*, Eds, O. Cohen-Haguenauer and M. Boiron, pp. 63–73, Editions John Libbey Eurotext, France; Glorioso, et al. 1995. *Herpes simplex virus as a gene-delivey vectors for the central nervous system. In: Viral Vectors-Gene therapy and neuroscience application*, Eds, M. G. Kaplitt and A. D. Loewy, pp. 1–23. Academic Press, New York). Vaccinia virus, of the poxvirus family, has also been developed as an expression vector (Smith, G. L., and B. Moss. 1983. *Infectious poxvirus vectors have capacity for at least 25,000 base pairs of foreign DNA. Gene* 25: 21–28; Moss, B. 1992. *Poxviruses as eukaryotic expression vectors. Semin. Virol.* 3: 277–283; Moss, B. 1992. *Poxviruses as eukaryotic expression vectors. Semin. Virol.* 3: 277–283). Each of the above-described vectors are widely available to one skilled in the art and would be suitable for use in the present invention.

Retroviral vectors are capable of infecting a large percentage of the target cells and integrating into the cell genome (Miller, A. D., and G. J. Rosman. 1989. *Improved retroviral vectors for gene therapy and expression. Biotechniques* 7: 980–990). Retroviruses were developed as gene transfer vectors relatively earlier than other viruses, and were first used successfully for gene marking and transducing the cDNA of adenosine deaminase (ADA) into human lymphocytes.

It is also possible to produce a viral vector in vivo by implantation of a "producer cell line" in proximity to the target cell population. As demonstrated by Oldfield, et al. (*Gene Therapy for the Treatment of Brain Tumors Using Intra-Tumoral Transduction with the Thymidine Kinase Gene and Intravenous Ganciclovir, Human Gene Therapy* 4:39–69), infiltration of a brain tumor with cells engineered to produce a viral vector carrying an effector gene results in the continuous release of the viral vector in the vacinity of the tumor cells for an extended period of time (i.e, several days). In such a system, the vector is retroviral vector which preferably infects proliferating cells, which, in the brian, would include mainly tumor cells. The present invention provides a methodology with which a viral vector supplies a nucleic acid sequence encoding a protein having sialyl-transferase activity to cells involved in a nuerological disorder such as brain cancer.

"Non-viral" delivery techniques that have been used or proposed for gene therapy include DNA-ligand complexes, adenovirus-ligand-DNA complexes, direct injection of DNA, $CaPO_4$ precipitation, gene gun techniques, electroporation, and lipofection (Mulligan, R. C. 1993. *The basic science of gene therapy. Science* 260: 926–932). Any of these methods are widely available to one skilled in the art and would be suitable for use in the present invention. Other suitable methods are available to one skilled in the art, and it is to be understood that the present invention may be accomplished using any of the available methods of transfection. Several such methodologies have been utilized by those skilled in the art with varying success (Mulligan, R. C. 1993. *The basic science of gene therapy. Science* 260: 926–932). Lipofection may be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

The cells may be transfected in vivo (preferably at the tumor site), ex vivo (following removal from a primary or metastatic tumor site), or in vitro. The cells may be transfected as primary cells isolated from a patient or a cell line derived from primary cells, and are not necessarily autologous to the patient to whom the cells are ultimately administered. Following ex vivo or in vitro transfection, the cells may be implanted into a host, preferably a patient having a neurological disorder and even more preferably a patient having a brain tumor. Genetic manipulation of primary tumor cells has been described previously (Patel et al., 1994. *Human Gene Therapy* 5, p. 577–584). Genetic modification of the cells may be accomplished using one or more techniques well known in the gene therapy field (*Human Gene Therapy*. April 1994. Vol. 5, p. 543–563; Mulligan, R. C. 1993. *The basic science of gene therapy. Science* 260: 926–932).

In order to obtain transcription of the nucleic acid of the present invention within a target cell, a transcriptional regulatory region capable of driving gene expression in the target cell is utilized. The transcriptional regulatory region may comprise a promoter, enhancer, silencer or repressor element and is functionally associated with a nucleic acid of the present invention. Preferably, the transcriptional regulatory region drives high level gene expression in the target cell. It is further preferred that the transcriptional regulatory region drives transcription in a cell involved in a neurological disorder such as brain cancer. Transcriptional regulatory regions suitable for use in the present invention include but are not limited to the human cytomegalovirus (CMV) immediate-early enhancer/promoter, the SV40 early enhancer/promoter, the JC polyomavirus promoter and the chicken β-actin promoter coupled to the CMV enhancer (Doll,et al. 1996. *Comparison of promoter strengths on gene delivery into mammalian brain cells using AAV vectors. Gene Therapy* 3: 437–447).

The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.). Examples of nucleic acid constructs useful for practicing the present invention comprise a transcriptional regulatory region such as the CMV immediate-early enhancer/promoter, the SV40 early enhancer/promoter, the JC polyomavirus promoter, or the chicken β-actin promoter coupled to the CMV enhancer operably linked to a nucleic acid comprising a sequence of Table 1. To generate such a construct, a nucleic acid sequence encoding the enzyme may be processed using one or more restriction enzymes such that certain sequences flank the nucleic acid. Processing of the nucleic acid may include the addition of linker or adapter sequences. A nucleic acid sequence comprising a preferred transcriptional regulatory region may be similarly processed such that the sequence has flanking sequences compatible with the nucleic acid sequence encoding the enzyme. These nucleic acid sequences may then be joined into a single construct by processing of the fragments with an enzyme such as DNA ligase. The joined fragment, comprising a transcriptional regulatory region operably linked to a nucleic acid comprising a sequence that is over- or underexpressed in a cancer cell, preferably being a sequence substantially identical to a sequence of Table 1 or SEQ ID NOS. 1–9, may then be inserted into a plasmid capable of being replicated in a host cell by further processing using one or more restriction enzymes.

Administration of a nucleic acid of the present invention to a target cell in vivo may be accomplished using any of a variety of techniques well known to those skilled in the art. Such reagents may be administered by intravenous injection or using a technique such as stereotactic injection to administer the reagent into the target cell or the surrounding areas (Badie, et al. 1994. *Stereotactic Delivery of a Recombinant Adenovirus into a C6 Glioma Cell Line in a Rat Brain Tumor Model. Neurosurgery* 35: 910; Perez-Cruet, et al. 1994. *Adenovirus-Mediated Gene Therapy of Experimental Gliomas. J. Neur. Res.* 39: 506; Chen, et al. 1994. *Gene therapy for brain tumors: Regression of experimental gliomas by adenovirus-mediated gene transfer in vivo.* Proc. Natl. Acad. Sci. USA 91: 3054; Oldfield, et al. 1993. *Gene Therapy for Treatment of Brain Tumors Using Intra-Tumoral Transduction with the Thymidine Kinase Gene and Intravenous Ganciclovir. Human Gene Therapy* 4:39–69; Okada, et al. 1996).

In another embodiment, the present invention provides a methodology for transfection of a functional nucleic acid sequence, preferably an antisense oligonucleotide, that inhibits expression of a nucleic acid comprising a sequence of Table I or a protein encoded by a nucleic acid comprising a sequence of Table I. The antisense oligonucleotide may comprise a functional nucleotide sequence such as a 2',5'-oligoadenylate as described in U.S. Pat. No. 5,583,032. Using such an antisense oligonucleotide, expression of a protein comprising a sequence substantially identical to that encoded by the sequences of Table I or SEQ ID NOS. 1–9 may be inhibited by inhibition of transcription, destruction of the transcript encoding the protein, or inhibition of translation of the protein from its transcript.

In certain embodiments of the present invention, transfection of a cell is performed. In a preferred embodiment, the cell is involved in the causation of a neurological disorder such as brain cancer, Parkinson's disease or Alzheimer's disease. In a preferred embodiment, the cell is a cancer cell, and in a more preferred embodiment, the cell is a brain cancer cell. More preferably, the nucleic acid comprises a sequence encoding the protein encoded by a nucleic acid comprising a sequence of Table I or SEQ ID NOS. 1–9 is under the transcriptional control of a transcriptional regulatory region which functions within a neural tissue or cell.

In another embodiment of the present invention, a target cell is transfected in vivo by implantation of a "producer cell line" in proximity to the target cell population (Oldfield, et al. 1993. *Gene Therapy for Treatment of Brain Tumors Using Intra-Tumoral Transduction with the Thymidine Kinase Gene and Intravenous Ganciclovir. Human Gene Therapy* 4:39–69; Culver, et al. 1994. *Gene Therapy for the Treatment of Malignant Brain Tumors with in vivo Tumor Transduction with the Herpes Simplex Thymidine Kinase Gene/Ganciclovir System, Human Gene Therapy* 5: 343–379). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the product of nucleic acid of the present invention occurs. Preferably, expression results in either increased or decreased expression of a protein encoded by the nucleic acid, which preferably comprising substantially identical DNA sequence to the sequences of Table I or SEQ ID NOS. 1–9.

In yet another embodiment, the present invention comprises a kit for determining the tumorigenicity or malignancy of a brain cell. The kit may comprise a panel of independent or paired nucleic acid molecules specific for the detection of the expression of specific nucleic acid sequences corresponding to nucleic acid sequences that are over- or underexpressed in cancer cells. Preferably, the sequences are substantially identical to those of Table I or SEQ ID Nos. 1–9. One embodiment of such a kit utilizes enzyme-mediated nucleic acid amplification such as the polymerase chain reaction (PCR) in which a pair of nucleic acid molecules (i.e., primers) that allow for amplification of a nucleic acid sequence of Table I.

c. Small Molecules

The methods and compositions of the present invention are useful for the manufacture of pharmaceuticals and therapeutics which encompass compounds that interact with or affect the expression of nucleic acid sequences or proteins over- or underexpressed in cancer cells. Preferably, the nucleic acid sequences comprise sequence substantially identical to those sequences listed in Table I or SEQ ID NOS. 1–9. Such inhibitors can take the form of traditional chemotherapeutic agents, as well as specific anti-sense nucleic acids targeted to the nuclei acid sequences. Such therapeutics can be directed against single nucleic acid targets, but most preferably are targeted at more than one specific nucleic acid sequence.

The invention provides for such a method wherein said malignant biological sample is a biopsy sample from a patient to be treated, a cell line, cell. The present invention also provides for therapeutic compounds identified or otherwise identifiable by this method, and any compound corresponding to a compound identified by these methods. The reagents and methodologies of the present invention provide an assay system for determining the effect of a compound on gene expression in a cell. In one embodiment, the cell may be affected such that upon administration of the compound to a patient, cell growth or activity that may be detrimental to the patient may result. In such cases, it would be beneficial to have at the researcher's disposal a rapid, accurate, and efficient assay system to measure the likelihood that a compound may have such effects. Preferably, the "panel" refers to the sequences of Table I and SEQ ID Nos. 1–9, as well as fragments and other nucleic acids substantially identical to those sequences. It is to be understood by the skilled artisan that the present invention provides an assay or test system that is applicable to many types of cells and panels of nucleotide sequences.

In one embodiment, the present invention provides an assay for identifying a compound that may promote or prevent cancer. A method for identifying a compound affecting a cell is provided wherein a cell is contacted with a compound and expression of one or more nucleotide sequences or proteins selected from a panel of sequences is detected. The panel may consist of one or more sequences of the invention. The level of expression may be compared to control levels, such as where a cell has not been contacted by the compound but is otherwise maintained under identical conditions as the cell that has been contacted. In one embodiment, a method for detecting a compound that may promote cancer comprising detection of increased expression of the panel of sequences following contact of the cell with the compound is provided. In another embodiment, a method for detecting decreased expression of one or more members of the panel of sequences following exposure to the compound, thus identifying a compound that may inhibit tumor cell migration. In yet another embodiment, a method for detecting increased expression of the one or more members of the panel following exposure to the compound, thus identifying a compound that may promote tumor cell migration. In a preferred embodiment, the present invention provides an assay for identifying a compound that may promote or prevent brain cancer. In one embodiment, the sequences are selected from sequences substantially identical to those sequences in Table I or SEQ ID Nos. 1–9, fragments thereof, or sequences substantially similar to those sequences. Any combination of such sequences may be combined to provide a useful assay system as described herein.

In one embodiment of the present invention, a method for identifying a compound affecting a cell is provided wherein a cell is contacted with a compound and expression of a reporter gene functionally linked to a transcriptional regulatory sequence of a nucleotide sequence that is up- or down-regulated in cancer cells. In a preferred embodiment, the reporter sequences is β-galactosidase, luciferase, green fluorescent protein or chloramphenicol acetyl transferase (CAT). In a preferred embodiment, the transcriptional regulatory region controls the expression of a sequence substantially identical to a sequence of Table I or SEQ ID NOS. 1–9.

In yet another embodiment, the present invention comprises a kit for determining the effect of a compound on gene expression within a cell. The kit may comprise packaged reagents such as a panel of independent or paired nucleic acid molecules specific for the detection of the expression of specific nucleic acid sequences corresponding to specific species of nucleic acid sequences encoding proteins of interest. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like.

In another embodiment, the present invention provides a compound identified by its ability to cause an increase or a decrease in one or more sequences of a panel of sequences. The compounds of this invention may be formulated into diagnostic and therapeutic compositions for in vivo or in vitro use. Representative methods of formulation may be found in *Remington: The Science and Practice of Pharmacy*, 19th ed., Mack Publishing Co., Easton, Pa. (1995). For in vivo use, the compound may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

The pharmaceutically active compounds (i.e., polypeptides, nucleic acids, compounds or vectors) of this invention can be processed in accordance with conventional methods of pharmacy to produce medicinal agents for administration to patients, including humans and other mammals. For oral administration, the pharmaceutical composition may be in the form of, for example, a capsule, a tablet, a suspension, or liquid. The pharmaceutical composition is preferably made in the form of a dosage unit containing a given amount of DNA or viral vector particles (collectively referred to as "vector"). For example, these may contain an amount of vector from about $10^3$–$10^{15}$ viral particles, preferably from about $10^6$–$10^{12}$ viral particles. A suitable daily dose for a human or other mammal may vary widely depending on the condition of the patient and other factors, but, once again, can be determined using routine methods. The vector may also be administered by injection as a composition with suitable carriers including saline, dextrose, or water.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A suitable topical dose of active ingredient of a vector of the present invention is administered one to four, preferably two or three times daily. For topical administration, the vector may comprise from 0.001% to 10% w/w, e.g., from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

The compositions of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrastemal, infusion techniques or intraperitoneally. Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The dosage regimen for compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

While the compounds, polypeptides, nucleic acids and/or vectors of the invention can be administered as the sole active pharmaceutical agent, they can also be used in combination with one or more vectors of the invention or other agents. When administered as a combination, the therapeutic agents can be formulated as separate compositions that are given at the same time or different times, or the therapeutic agents can be given as a single composition.

VI. Conclusions

Thus the compositions and methods of the present invention are useful as clinical screens for the specific diagnosis and identification of cancer. Preferably, the cancer is brain cancer, and more preferably, the cancer is glioma. In one embodiment, the strong indication of glioma is characterized by detection of increased expression of all nine nucleic acids of Table I and SEQ ID Nos. 1–9. The methods and assays of the invention are also useful for the detection of potential cancer development such as glioma, as in the case where, for example, less than nine nucleic acids of Table I and SEQ ID Nos. 1–9 are detected. Thus the determination and early detection of glioma propensity greatly assists the medical practitioner and patient decide upon the proper course of action. Once such action is taken, the methods of the present invention allows for the monitoring of recurrence after surgery, or during the course of chemotherapy.

The following Examples are for illustrative purposes only and are not intended, nor should they be construed as limiting the invention in any manner. Those skilled in the art will appreciate that variations and modifications can be made without violating the spirit or scope of the invention.

EXAMPLES

As discussed above, DDRT-PCR has become one of the more powerful methods to identify and analyze altered gene expression at the mRNA level. It has been utilized to identify cellular mRNAs whose expression is altered in malignant brain tumors, and has successfully yielded several genes. Most of these to date are still of unknown function and clinical utility. Established herein is a reliable DDRT-PCR/screening protocol to study modulation of gene expression in human brain tumors. A comparison between cultured NHFA and a tumorigenic glioma cell line, U373MG was initially chosen for study. This system provided a proliferative model of glial lineage which supplied both well-defined and renewable resources necessary for our intensive screening protocols. Following DDRT-PCR using a panel of 84 unique primer pairs, differentially expressed amplicons were further screened by a series of Northern analyses. As described below, comparison of cultured normal human fetal astrocytes (NHFA) with a tumorigenic glioma cell line (U373MG) initially generated at least 167 differentially expressed transcripts, wherein at least 61 mRNAs appeared to be uniquely expressed in the malignant cells. Ultimately, by performing tissue-based secondary screens, employing Reverse Northern analysis, a unique subset of 9 signals was identified and characterized.

Example 1

Isolation of RNA

1. Cell Culture and Brain Tumor Specimens

Human glioblastoma cell line U373MG (American Type Culture Collection—ATCC, Manassas, Va.) was the source of malignant phenotype expression signals. Cultured normal human fetal astrocytes, isolated according to Yamamoto et al., (1997, *Brain Research* 755(1):175–9), and processed no later than 20 passages from the initial isolation, was the source of normal tissue expression signals. All cells were subcultured in Dulbeccos Modified Eagles Medium (DMEM) containing 10% heat-inactivated fetal bovine serum (FBS; Whittaker BioProducts, Walkersville, Md.), penicillin/streptomycin and glutamine and were maintained in log phase at 37° C. in the presence of 10% $CO_2$.

The material for the secondary clinical reverse northern screens was obtained with informed consent from two sources: (1) normal human brain tissue was obtained from the Brain and Tissue Bank for Developmental Disorders at the University of Maryland, (Baltimore, Md.), (2) human brain tumor tissue, from donor tissue, glioblastoma multiforme, recurrent glioblastoma multiforme, and astrocytoma grade IV (glioblastoma) was obtained from excised tumor material. The clinical material,as classified according to WHO Brain Tumor Classification, are all treated as glioblastoma tissue.

Briefly, total RNA was extracted from tissues by guanidinium thiocyanate treatment, followed by separation using cesium chloride centrifugal sedimentation, and treated with DNase I for 30 minutes at 37° C.

RT-PCR was performed on the extracted RNA using commercially availible oligonucleotide primers, following the recommended procedures. Specifically, anchored primers and 20 arbitrary 10-mer primers from Operon Technologies, Inc. (Kit A; Alemeda, Calif.), and 8 arbitrary 13-mer primers from GenHunter Corp. (Cat. No. H-AP-D; Brookline, Mass.) were selected. Specifically, the primers were:

Anchored Primer $T_{11}M$ (where M is A, C or G)

Random Primer

Operon Technologies, Kit A, primers OPA-01 to OPA-20

GenHunter Corp., H-AP primer set 4, primers H-AP25 to H=AP32

The combination of the primers from these two commercial kits produce a total of 84 unique primer pairs. Differential display was performed essentially as described by Liang et al., (1992, *Science*, 257:967–71). For each of the three anchored primers in each sample, 0.2 ug of total DNA-free RNA was reverse transcribed with 50U Maloney Murine Lukemia Virus (MMLV) reverse transcriptase in the presence of 200 pmol anchored primer, and 20 uM dNTP for 5 minutes at 65° C., followed by 60 minutes at 37° C. Following heat inactivation of the reverse transcriptase at 75° C. for 5 minutes, 2 $\mu$l of the RT mixture was amplified in the presence of 2 uM dNTP, 200 nM of the appropriate anchored primer, 4 pmol arbitrary (random) primer, 10 uCi $\alpha$-[$^{32}$P]dATP (1000–3000 Ci/mmol; Amersham Corp., Arlington Hts., Ill.), and 1 Unit of AmpliTaq® (T. aqut. DNA polymerase; Perkin-Elmer Corp., Branchburg, N.J.). The cycling parameters were: 94° C. for 15 sec., 40° C. for 2 min., 72° C. for 30 sec., for 40 cycles. Following a final extension for 5 min. at 72° C., the samples were stored at 4° C. until analysis. The PCR products were electrophoresed on 6% sequencing gels. Differentially expressed bands of interest were excised from the dried gel, boiled in $dH_2O$, purified by ethanol precipitation, and reconstituted in 10 $\mu$l $dH_2O$.

The minimal selection criteria for the bands of interest was approximately two-fold greater signal expressed in either tissue, and was qualitatively evaluated by visual inspection of the autoradiographic image.

Example 2

Screening of RNA

A 4 $\mu$l aliquot of the purified cDNA amplicons were then reamplified, using similar conditions as described above, without radioactive isotope, and in the presence of 20 uM dNTP. Following electrophoresis through 1.5–2.0% agarose, the amplicons were purified using QIAquick® gel extraction (Qiagen, Inc., Valencia, Calif.) and reconstituted in a total volume of 40 ul. Duplicate 4 $\mu$l aliquots of this gel purified cDNA were reamplified and combined in a total volume of 150 $\mu$l for reverse Northern analysis. To this sample, 6 $\mu$l of 10N NaOH was added, and the mixture was incubated at 4° C. for 10 minutes to denature the nucleic acids. The mixture was then diluted 1:1 with 150 $\mu$l of 2 M $NH_4OAc$, 150 $\mu$l of which was applied to duplicate nylon membranes presoaked with 1 M $NH_4OAc$. Wells of the slot-blot apparatus (Schleicher & Schuell, Keene, N.Y.) were washed with 150 $\mu$l of 1 M $NH_4OAc$ and filters rinsed in 6x SSC and soaked for 15 minutes in 2x Denhardt's solution, and air dried. The filters were UV-crosslinked in a Stratlinker apparatus (Stratagene, LaJolla, Calif.), and prehybridized for 2–4 hours at 57° C. in 10% dextran sulfate, 1 M NaCl, 1% SDS, and 50 ug/ml sheared salmon sperm DNA. The radiolabeled probe was prepared by reverse transcription (RT) of 10 ug total RNA from normal fetal astrocytes, or glioma cell line U373MG cells, utilizing the above conditions. Following RT, probe was treated with 20 ug RNase A for 30 minutes at 37° C. and purified by Sephadex G50 chromatography. Equivalent amounts of radiolabeled probe (2–3x10$^6$ cpm/ml) were added to the respective blots and hybridized overnight at 57° C. Blots were washed in 2x SSC/1% SDS at 57° C. for 30 minutes and autoradiographed for an appropriate time.

The minimal selection criteria for the bands of interest was approximately two-fold greater signal expressed in either tissue, and was qualitatively evaluated by visual inspection of the autoradiographic image.

The amplicons determined to be differentially expressed (either glioblastoma or normal brain tissue specific) were subsequently subcloned into the TA cloning site of the pCR(R)2.1 vector (Invitrogen, Carlsbad, Calif.) and insert-containing vectors from multiple positive transformants were sequenced using an ABI 377 automated fluorescence-based nucleic acid sequencer. All NCBI maintained nucleotide databases (National Center for Biotechnology Information; Bethesda, Md.) were searched for homologies using the BLAST (basic local alignment search tool) program.

Example 3

Further Selection of Characteristic RNA

Those mRNAs exhibiting differential expression following the reverse Northern screening were chosen for further detailed analysis using clinically relevent tissue and secondary reverse Northern analysis. Individual vector-bound cDNA inserts identified, subcloned and sequenced from the initial screen were linearized with an appropriate restriction enzyme and immobilized on each of six nylon membranes, as described above. The prepared membranes were individually hybridized with radiolabled probes prepared by reverse transcription of 10 ug total RNA from each of three normal brain tissue or three glioblastoma brain tissue samples. Following reverse transcription, the probes were treated with 20 ug RNase A for 30 minutes at 37° C. and purified by Sephadex G50 chromatography. Equivalent amounts of radiolabeled probe ($1.1-1.2 \times 10^6$ cpm/ml) were added to the respective blots and hybridized overnight at 57° C. Blots were washed in 2× SSC/1% SDS at 57° C. for 30 minutes and analyzed by Phosphor Imaging for 48 hours.

Individual radioactive signals on the blots were quantitated using BioRad Model GS-250 Molecular Imager(R) System and Molecular Analyst(TM)/Macintosh Image Analysis Software (Version 2.1). One-dimensional profiles were optimized by subtracting image background, as well as pGEM(R) vector control value. An independent Student's t-test was performed comparing the peak heights (in counts) of the three glioblastoma blots, and the three normal brain tissue blots, for each differentially expressed cDNA using SigmaPlot 5.0.

Example 4

Sequencing of Characteristic Signal cDNA Inserts

The probes selected above as characteristic signals can then be used to identify gene sequences by screening human cDNA libraries.

For example approximately $2 \times 10^6$ independent clones from a lambda-gt-11 oligo(dT)+random primed human fetal cDNA library (Clontech, Palo Alto, Calif.) were screened with radiolabeled amplicons from two of the selected differentially expressed characteristic signals identified above, in order to determine the gene sequence. (CINN1 and CINN2)

Positive plaques were purified by additional screening, and the inserts isolated by subcloning into pGEM(R)7zf(-) vector, sequenced and individually utilized in reverse Northern screening of clinical tissues. The isolated and cloned nucleic acid signals corresponding to the expressed genes listed in Table I below identifies the characteristic signals of the invention. Known genes, and the complete nucleic acid sequence for such genes can be obtained from the art, and detection probes designed to specifically identify the expression of such genes in biological samples. In particular, once known, one of ordinary skill in the art can readily identify and prepare hybridization probes which will be suitable for the specific hybridization detection of the desired gene transcript, under a variety of hybridization conditions (see eg. *Molecular Cloning* supra). One of skill in the art will be a able to select and prepare suitable PCR primers for primer specific amplification of the desired gene transcript. Such primers can be designed to utilize the poly-A tail present on such transcripts, so as to specifically identify transcription products. Inserts identified as novel genes can be further cloned and expanded such that a complete nucleic acid sequence is obtained (see Example 7 below). However, one of skill in the art will be able to use the nucleic acid sequence of the novel inserts identified in Table I, to construct suitable hybridization probes, as well as PCR primers for use in specifically identifying transcripts corresponding to the novel gene represented by the insert.

The characteristic signals listed in Table I and SEQ ID Nos. 1–9 are not limited to just these signals, as other further characterizing gene transcripts may also be identified and detected in addition to any one or more of the characteristic signals identified in the Table below.

TABLE I

Characteristic Gene Expression

| cDNA name | Genbank ID | NL[1] | GBM[2] | |
|---|---|---|---|---|
| CINN 1 | novel | 36 ± 63 | 902 ± 454 | (SEQ ID NO.:8) |
| CINN 2 | dek | 1018 ± 1268 | 5422 ± 2046 | (SEQ ID NO.:9) |
| OP2 C2-6 | Lmα-chain | 1472 ± 1024 | 7862 ± 3416 | (SEQ ID NO.:1) |
| OP7 C3-1 | α-NAC | 787 ± 670 | 5000 ± 2367 | (SEQ ID NO.:2) |
| OP9 A4-2 | rib.L35a | 1748 ± 581 | 5004 ± 1818 | (SEQ ID NO.:3) |
| OP11 C1-3 | novel | 262 ± 257 | 899 ± 250 | (SEQ ID NO.:4) |
| OP11 G2-10 | rib.L7a | 730 ± 384 | 6929 ± 1014 | (SEQ ID NO.:5) |
| FAS OP13 | novel | 495 ± 301 | 1736 ± 629 | (SEQ ID NO.:6) |
| FAS OP17 | novel | 52 ± 90 | 1051 ± 466 | (SEQ ID NO.:7) |
| HHCJ32 | α-Tubulin[3] | 6716 ± 3538 | 58048 ± 2815 | |

[1]Normal brain tissue
[2]Glioblastoma Cells
[3]Control gene

Example 5

Cloning of Identified Genes

The novel gene insert named CINN-1 was cloned, isolated and sequenced using standard techniques. The nucleic acid sequence depicted in FIG. 1.

The present invention provides for the novel gene CINN-1 having the nucleic acid sequence depicted in FIG. 1. One of ordinary skill in the art will be able to prepare further embodiments incorporating the CINN-1 gene into expression vectors for the generation of recombinant protein in prokaryotic or eukaryotic expression systems known in the art, using transformed host cells such as insect cells, bacterial cells and mammalian cells. (See eg. *Gene Expression Technology* supra). Once such protein is obtained, it is then possible to generate mammalian antibodies that specifically bind to the CINN-1 protien product. Such antibodies can be generated in mice, rats, rabbits, goats, pigs, hamsters etc., as polyclonal antiserum, and further used to generate CINN-1 protein specific monoclonal antibodies. One of skill in the art would then be able to generate modified antibody protein so as generate humanized monoclonal antibodies. It is also within the skill of those in the art to generate protein from the novel inserts described in Table I, and prepare antibodies specific for the translated insert proteins corresponding to the nucleic acids therein.

For example, the nuclei acids described as SEQ ID NO. 1–9 can be expressed in appropriate reading frames to generate protein, using expression systems known in the art.

These recombinant proteins can be used to generate antibodies specific thereto, using methods known in the art. In addition, fragments of the nucleic acid sequences described in SEQ ID NO. 1–9 can be used to generate peptide fragments as well. Peptide fragments of at least 7 amino acid residues in length can be made immunogenic and generate antibodies specific for such peptides. Following identification and isolation of antibody specific for the proteins of the invention, the antibodies can be employed in protein purification, detection assays, and as therapeutic agents using methods that are known in the art.

Example 6

Differntial Expression of Dek mRNA in Human Brain Tumors dek encodes a 43 kD nuclear phosphoprotein of unknown function, and is expressed in a subset of patients with acute myeloid leukemia as a fusion protein formed through reciprocal translocation. This fusion protein contains the majority of the dek gene at its N-terminus fused to the 3' end of another gene, can. The function of the dek-can fusion protein in these tumors is unknown. dek has also been described as a major immunoreactive antigen in patients with autoimmune diseases, such as juvenile rheumatoid arthritis, lupus erythematosis, and Kikuchi's disease. Additionally, the ability of dek to complement Ataxia-Telangietasia (Group D) fibroblasts has been described. Recently, dek has been demonstrated to be a sequence-specific DNA binding protein. It binds to the TG-rich peri-ets (pets) element (5'-TTGGTCAGGG-3') in the HIV-2 enhancer, mediating transcriptional activation in response to T-cell activation. Sequences highly homologous to these dek binding sites have been found in some early myeloid genes, such as neutrophil elastase and myeloperoxidase. Characterization of the expression and function of dek in brain tumors will allow us to better understand the basic nature of the malignancy.

A. MATERIALS AND METHODS

Tissue and Cell Lines

For the Differential Display analysis, U373MG, a human Grade III astrocytoma cell line obtained from ATCC (Rockville, Md.), and human fetal astrocytes obtained from V. W. Yong, University of Calgary, Alberta, Canada, were utilized. Additional tumor cell lines were purchased from ATCC. All cell lines were routinely subcultured in Dulbecco's Modification of Eagles Medium (DMEM) containing 10% heat-inactivated fetal bovine serum, penicillin/streptomycin and glutamine and were maintained in log phase at 37° C. in the presence of 10% $CO_2$. Fetal astrocytes were processed at no later than 20 passages from initial isolation. Normal human brain tissue was obtained from the Brain and Tissue Bank for Developmental Disorders at the University of Maryland, Baltimore, Md. Brain tumor tissue was obtained from the tumor bank maintained by CINN.

Differential Display

Total RNA was extracted by guanidinium thiocyanate followed by cesium chloride sedimentation (Chirgwin, et.al.) and treated with DNase I. Reverse transcription was performed utilizing single base anchored primers: ($T_{11}M_n$, 5' TTTTTTTTTTTM 3', where M denotes A, C, or G). Differential display was performed essentially as described (Liang, et.al., 1992). For each of the three anchored primers in each sample, 28 arbitrary upstream primers were utilized in the PCR amplification to produce a total of 84 unique primer pairs in the analysis. The resultant amplicons were electrophoresed on 6% sequencing gels. Differentially expressed amplicons were excised, reamplified and purified prior to sequential Reverse Northern analysis. They were immobilized on duplicate nylon slot blot membranes and hybridized with radiolabeled cDNA prepared from total RNA from fetal astrocytes, U373MG cells, or from clinical material as probes. Those confirming differential expression following these sequential screens were subsequently subcloned into the TA cloning site of the pCR®2.1 vector (Invitrogen, Carlsbad, Calif.) and insert-containing vectors from multiple positive transformants sequenced using an ABI 377 automated fluorescence-based sequencer. All NCBI maintained nucleotide databases (National Center for Biotechnology Information, Bethesda, Md.) were searched for homologies using the BLAST algorithm (http//www.ncbi.nlm.nih.gov/BLAST/index.html).

Northern Blot Analysis

25 µg of total RNA isolated as above was electrophoresed through 1.2% formaldehyde-agarose gels and transferred to nylon membranes by capillary blotting. The membrane was hybridized to a uniformly [$^{32}P$]-labeled cDNA amplicon identified by differential display. This probe is homologous to the 3'end of the dek protein coding region. Filters were hybridized for 90 minutes at 68° C. using Express-Hyb (Clontech, Palo Alto, Calif.). Filters were washed in 0.1× SSPE/0.1% SDS at 50° C. and analyzed by autoradiography for appropriate times.

SDS/PAGE and Western Analysis

Cells were scraped, pelleted and lysed in a buffer containing 62.5 mM Tris (pH 6.8), 2% SDS, 5% glycerol, and 1% β-mercaptoethanol. 20 µg of whole cell lysate protein from each cell line was electrophoresed through 8% polyacrylamide gels and electrophoretically transferred to nylon membranes in a buffer containing 25 mM glycine, 192 mM Tris base and 20% methanol. Membranes were blocked for 1 hour at 25° C. in a buffer containing 5% nonfat dry milk, 10 mM Tris (pH 7.5), 100 mM NaCl, and 0.1% Tween 20 followed by incubation in a 1:500 dilution of primary monoclonal antibody against human dek (Transduction Laboratories, Lexington, Ky.). Subsequent to room temperature incubation in a 1:1000 dilution of secondary antibody (horseradish peroxidase-conjugated sheep anti-mouse Ig, Amersham, Arlington Heights, Ill.) for 1 hour, dek immunoreactive band was visualized by enhanced chemiluminescence (ECL) detection (Amersham).

Preparation of Whole Cell Extracts and Gel Mobility Shift Assay

Cells were scraped, pelleted, and flash frozen at −70° C. The frozen pellet was resuspended in a buffer containing 20 mM HEPES (pH 7.9), 25% glycerol, 420 mM NaCl, 1.5 mM $MgCl_2$, 0.2 mM EDTA, 0.5 mM DTT, and 0.5 mM PMSF and centrifuged at 100,000×g for 5 minutes at 4° C. The supernatants were assessed for basal dek binding activity. Binding reactions were performed by addition of 10 µg whole cell extract protein to a [$^{32}P$]-labeled 42-mer double-stranded oligonucleotide (ClaI/XbaI restriction fragment) containing a single dek-responsive pets binding sequence (5'-CGATCCAGCTATACTTGGTCAGGGCGAATTCT AACTATCTAG- 3') in 25 µl of binding buffer [10 mM Tris (pH 7.8), 50 mM NaCl, 1 mM EDTA, 0.5 mM DTT, 5% glycerol, 10 µg BSA, 0.5 µg poly(dI)poly(dC)]. Oligonucleotide was radiolabeled by filling in recessed ends with Klenow fragment of DNA polymerase I in the presence of [α-$^{32}P$]dCTP. Following incubation at 25° C. for 20 minutes, the protein-bound and unbound (free) oligonucleotides were electrophoretically separated in a nondenaturing 4% polyacrylamide gel in 6.7 mM Tris (pH 7.5)-1 mM EDTA-3.3 mM sodium acetate. Gels were dried and processed by autoradiography. For the competition experiments, the binding reaction mixtures contained either a 100-fold molar excess of an unlabeled pets oligonucleotide (self competition) or a 100-fold molar excess of an unlabeled consensus SP1 element oligonucleotide (5'-GCTCGCCCCGCCCCGATCGAAT-3') (non-self competition).

Plasmid Construction

Double-stranded pets element was derived by annealing complementary oligonucleotides (5'-ATCCAGCTAT ACTTGGTCAGGGCGAATTCTAACT-3' and 5'-AGTTAGAATTCGCCCTGACCAAGTATAGCTGGAT-3') followed by cloning of single (D1) or 2x multimerized (D2) pets element into the blunted ClaI/XbaI site of pGEM®7zF(−) (Promega, Madison, Wis.). The parental PCAT® Reporter vectors (Promega, Madison, Wis.) were utilized to evaluate the transcriptional activity of the pets consensus element in U373MG human glioma cells. Constructs denoted pD1.promoter and pD2.promoter replace the functional SV40 promoter with the single or 2x multimerized pets element cloned into the HindIII/XbaI site of pCAT®-Enhancer Vector. Constructs denoted pD1.enhancer and pD2.enhancer replace the functional SV40 enhancer with the single or 2x multimerized pets element cloned into the BamHI/XbaI site of pCAT®-Promoter Vector. Chloramphenicol Acetyltransferase (CAT) activity in cells transiently transfected with these constructs is dependent on insertion of functional promoter or enhancer sequences upstream or downstream from the CAT gene.

Transient Transfection Analysis

One day prior to transfection, cells were plated at approximately $3 \times 10^6$ cells per 100 mm dish. Cells were transiently transfected with 10 μg of each construct using a cationic liposome system, DOTAP (Boehringer-Mannheim), according to manufacturers specifications. 48 hours after transfection, whole cell lysate protein was isolated by multiple freeze-thaw cycles. CAT enzyme activity in 30 μg of lysate protein was measured following a 20 hour incubation at 37° C. in the presence of 40 μM [$^3$H]-labeled chloramphenicol and 240 μM n-butyryl Coenzyme A by liquid scintillation counting of xylene-soluble n-butyrylated chloramphenicol product.

B. RESULTS

A comprehensive and sensitive mRNA Differential Display Reverse Transcriptase Polymerase Chain Reaction (DDRT-PCR)/screening protocol to study modulation of the approximately 20,000 genes expressed in human brain tumors has been established herein. The initial system, comparing cultured normal human astrocytes with a tumorigenic glioma cell line, U373MG, provided a proliferative model of purely glial lineage. It also provided well-defined and renewable resources for intensive screening protocols. Sample mRNAs were extracted, reverse transcribed, and amplified by PCR using appropriate primers. The cDNA electrophoretic bands, or amplicons, that were different on the basis of their qualitative expression were excised from the gels and reamplified. Each of these sequences was subsequently sieved through our primary Reverse Northern screen for the capacity to hybridize to RNA preparations from the original material. We confirmed 41 mRNAs uniquely expressed in either normal human astrocytes or the U373MG cell line. We then developed and utilized a tissue-based secondary screen consisting of Reverse Northern analysis of the expression of these 61 genes with RNA isolated from normal brain and from tumor specimens resected from patients diagnosed with high grade glioma. A panel of 9 genes that demonstrate significantly elevated expression in, and are diagnostic for, high grade glial tumors were identified. Four of these genes are known and have been previously cloned. Their association with brain tumors, however, has not been described. Five of these genes are novel genes whose roles in glioma formation are currently under investigation. The approach provides a well-defined system for the identification of differentially expressed genes. It is the foundation of our understanding of the role of known genes and novel genes in the formation of brain tumors.

Among the 5 clinically relevant known genes, the dek gene was further characterized, based primarily on many of its known biological properties. dek is a putative oncogene encoding a nuclear protein that may function as a DNA binding/transcription factor. A unique profile of dek expression has been determined in brain tumors (FIG. 3). Panel A depicts Northern analyses of dek mRNA expression in a panel of gliomas of increasing grade. dek expression directly correlated with glioma grade, with robust expression in all of the higher grade tumors. dek expression was also robust in all of the glioma cell lines analyzed (FIG. 3B). Interestingly, overexpression of dek mRNA was not universal in neuroblastoma cell lines. Its expression in other types of brain tumors, such as metastases, Schwannoma, and different grades of meningioma is shown in the Appendix Figure. In contrast to high grade gliomas, dek mRNA was expressed at relatively low levels in most of these other brain tumors. These data demonstrate that dek expression is elevated in a distinct subset of brain tumors, namely those of glial origin. dek mRNA is also robustly expressed in human breast tumors and a number of human cell lines isolated from various tumor types (Appendix Figure).

FIG. 3C depicts dek protein levels in glioma cell lines. The robust expression of dek protein paralleled its RNA expression in glioma cell lines, when compared to that observed in normal brain.

Figure 4:
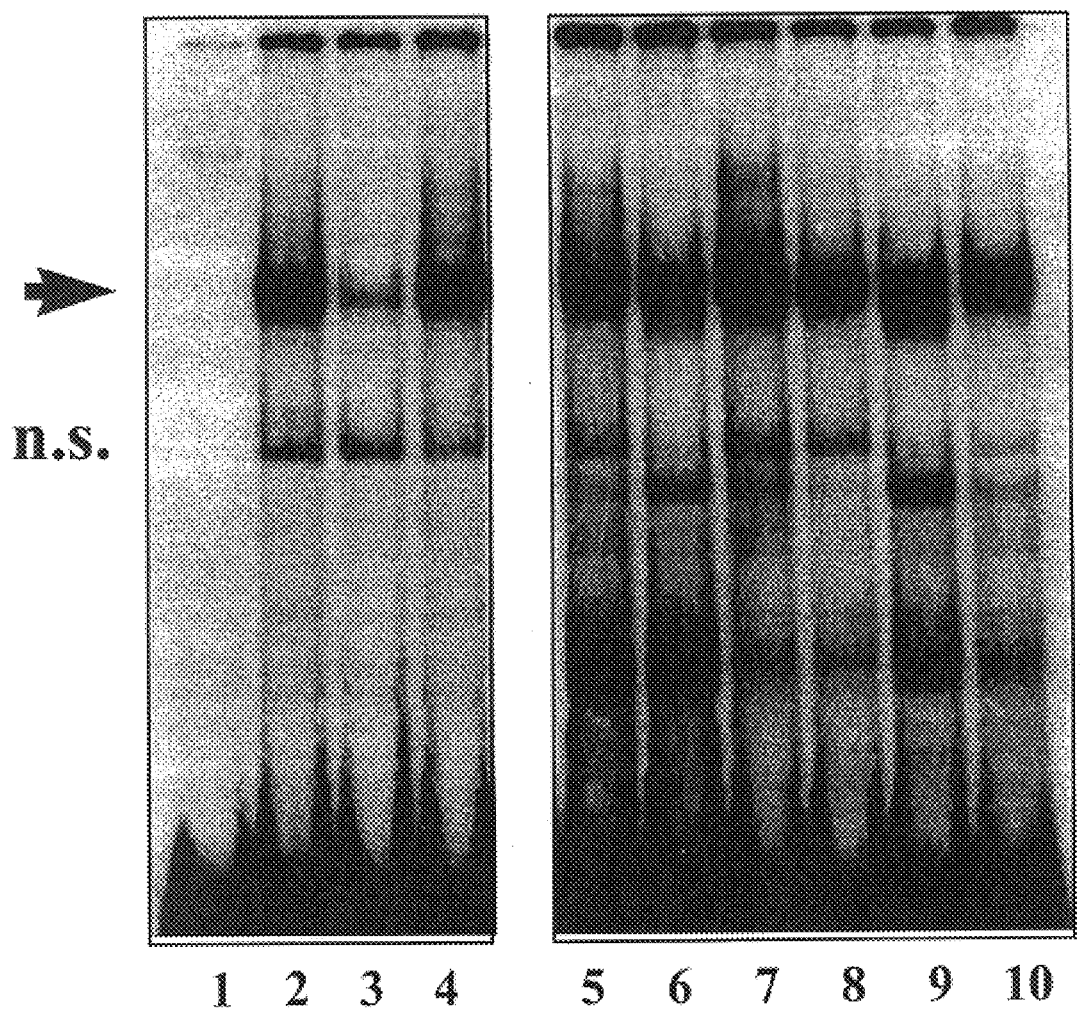
FIG. 4 depicts a gel mobility shift analysis of basal dek binding activity. 10 μg of protein extract from each cell line was incubated with a double-stranded, $^{32}$P-labeled oligonucleotide containing pets consensus sequences. The protein-bound and unbound (free) oligonucleotides were separated by electrophoresis through a 4% nondenaturing polyacrylamide gel and then detected by autoradiography. Lanes: 1, no protein; 2, 10 μg of U87MG protein extract; 3, U87MG extract preincubated with excess cold pets oligonucleotide (specific competitor); 4, U87MG extract preincubated with excess cold SP1 element oligonucleotide (nonspecific competitor); lanes 5 to 10; 10 μg of protein extract from U251, U373MG, U 118MG, D54, SW1088, and SNB19, respectively.

The observation that dek possesses the ability to bind to specific regions of DNA in glioma cells is consistent with its function as a transcription factor. The activity of dek protein was measured by its ability to bind to the pets element in a gel migration shift assay. The migration of free, unbound DNA through a gel is distinct from that of DNA bound to dek. FIG. 4 demonstrates the presence and specificity of this binding using cold, unlabeled oligonucleotide competitors. Addition of unlabeled pets site oligonucleotide competed away the binding (lane 3), while an unrelated oligonucleotide did not compete away the band (lane 4). The fact that dek is a transcription factor and is found primarily in tumors of glial origin suggests that it is important in regulating glioma-associated gene expression.

Figure 5:
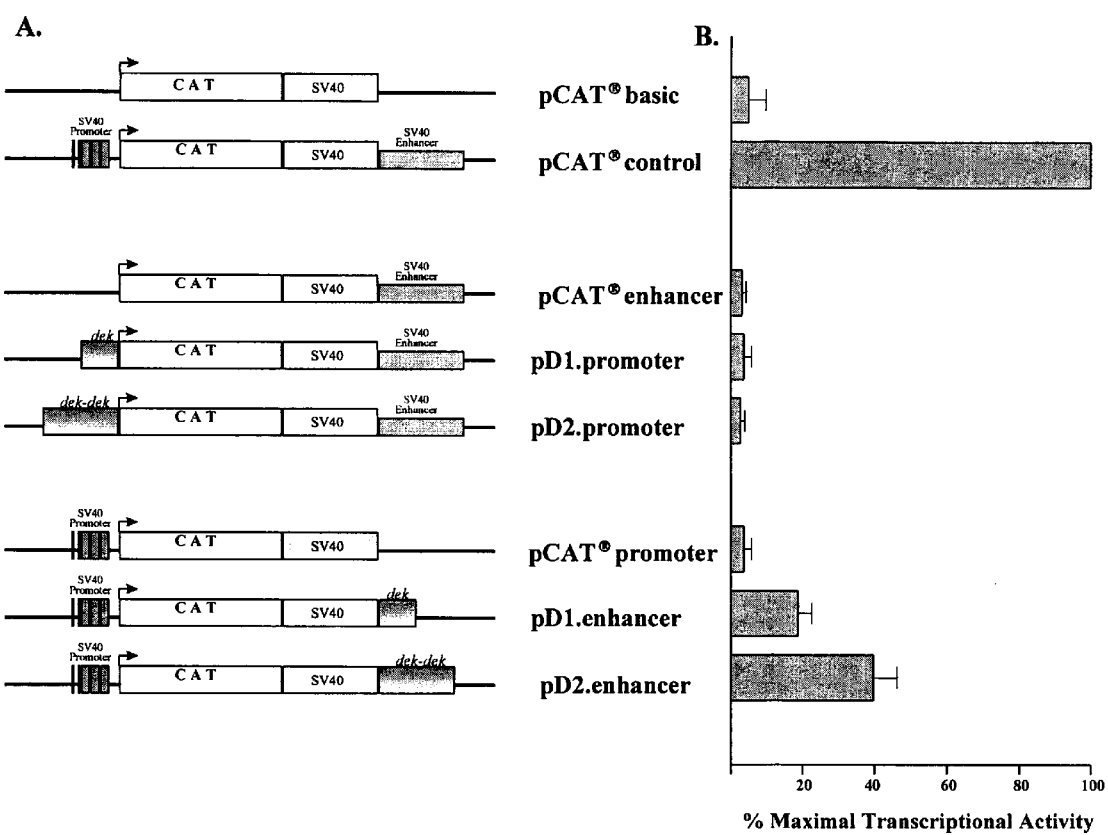
FIG. 5 depicts the transcriptional activity of the dek-responsive pets element in U373MG cells. A) dek/promoter and dek/enhancer constructs. Cells were transiently transfected with each of these constructs using a cationic liposome system, DOTAP, as described. Whole cell lysate protein was isolated 48 hours after transfection by multiple freeze-thaw cycles. B). Analysis of CAT enzyme activity. 30

The ability of dek to serve as a transcriptional regulatory element in gliomas was evaluated in a series of reporter gene analyses. Single and multiple copies of the dek-responsive pets element were inserted either 5' or 3' to the chloramphenicol acetyltransferase (CAT) gene in the context of SV40 elements to assess dek's strength as a promoter or as an enhancer element, respectively (FIG. 5A). The transcriptional effects upon CAT reporter gene expression following transfection of these constructs into U7373 cells are depicted in FIG. 5B. Neither the single (pD1.promoter) nor the double (pD2.promoter) pets element appear able to substitute for a functional promoter, as CAT transcriptional activity does not differ from background (pCAT® basic). Its ability to serve as an enhancer element, however, appears to correlate with number of binding sites. The level of transcriptional activity was approximately 20–40% of the activity measured in the presence of a fully functional SV40 promoter and enhancer (PCAT® control).

In conclusion, overexpression of dek mRNA was consistently observed in high grade gliomas but not in other brain tumors such as meningiomas or metastases from distant primaries. dek overexpression is observed in all glioma cell lines, and not in a majority of neuroblastoma cell lines. Similar levels of dek overexpression are observed in tumor cell lines derived from other tissues, and in primary breast tumors and metastases. This suggests that dek overexpression may play a role in cancers other than those of the brain. It was also determined that dek binds to DNA and functions as a potent transcriptional enhancer in glioma cells via its ability to bind to the pets consensus element. These studies suggest that strategies to down-regulate dek expression (e.g. antisense, ribozyme) or interfere with its function (e.g. transcription factor binding site decoys) may provide effective therapies for tumors that overexpress dek. In addition, it may be preferable to use the pets element in the context of various promoters (e.g. SV40, CMV) and/or other transcription factor binding sites (e.g. ets family) to confer glioma-specificity to gene therapy vectors. And, the elevated expression dek may lead to production of autoantibodies in the serum of glioma patients providing a basis for the development of a non-invasive diagnostic test for the presence of gliomas.

Example 7

Kit and Screening Assay for Characteristic Nucleic Acids

The characteristic diagnostic signal probes, being selected and identified above, are readily adaptable for use in production of screening assay kits. Such kits can include pre-packaged nucleic acid probes corresponding to at least a fragment of the above identified panel sequences, wherein when the assay kit is designed for hybridization detection, such probes are preferably from 10 to 25 nucleic acids in length.

Diagnostic/detection kits designed for use in hybridization and/or PCR based detection of signals can include appropriate paired primers that are specific for the nucleic acid sequences of the characteristic signals identified above, wherein said primers can be preferably 10 to 20 nucleic acids in length, or as suitable for use in automated detection apparatus. One of ordinary skill in the art would be able to design appropriate probes and PCR primers for the selective identification of the specific characteristic signals as listed in Table I, and using corresponding modified nucleic acids as desired. One of skill in the art will be further able to design specific PCR primers which will allow for the identification of actively transcribed genes by using the poly-A tail of such transcripts as a primer target, or as a partially anchored primer target. One of ordinary skill in the art would be able to generate suitable primers, and select appropriate amplification conditions and schemes to practice the present invention, and make modifications thereto. (See for example McPherson et al., *PCR Volume* 1, Oxford University Press, (1991)).

The detection kits of the invention also provide for sets of primers or hybridization probes which can be used to detect specific nucleic acid signals corresponding to one or more of the characteristic signals identified in Table I and SEQ ID Nos. 1–9, where such primers or probes are designed to be used in individual reactions, sequential reactions, or combination reaction, using one or more of the primers or probes in the same reaction mixture.

The diagnostic kits of the invention can further encompass suitable buffers for rehydration of dried probes, or dilution of concentrated probe solutions, or for preparing test samples, as needed to accomplish the designated assays. Diagnostic kits can be further designed to provide only the specific primers needed for PCR amplification and detection of the specific signals.

Detection assays, and the kits incorporating such assays of the invention, need not provide detection of the entire panel of signals, but may be designed to provide for less than the entire nine signals. The assays and kits can incorporate appropriate positive and negative controls, such as the tublin gene, where such control is proliferation dependent, or proliferation independent in signal production. The assay probes designed for PCR can incorporate the appropriate reaction contols, where the absence of such a signal is an indication that said amplification assay physically failed.

Example 8

Screening and Selection of Anti-Cancer Drugs

Using cell cultures of brain cancer cells, or even individual cancer cells, selection of promising drug candidates, and the evaluation of efficacy of various anti-cancer drugs for treating such cancer can be performed in the laboratory, either manually or using automated apparatus. For example, glioblastoma cells, as described above can be administered various doses of anti-cancer drugs, and screened for expression of specific nucleic acid messages corresponding to the panel shown in Table I. Any changes in the expression, or expression levels of any species of nucleic acid from this panel, as compared with normal or control cancer cells, would indicate potential for the therapeutic.

Typical anti-cancer drugs which can be specifically screened include Cytarabine, Fludarabine, 5-Fluorouracil, 6-Mercaptopurine, Methotrexate, 6-Thioguanine, Bleomycin, Dactinomycin, Daunorubicin, Doxorubicin, Idarubicin, Plicamycin, Carmustine, Iomustine, Cyclophosphamide, Ifosfamide, Mechloroethamine, Streptozotocin, Navelbine, Paclitaxel, Vinblastine, Vincristine, Asparaginase, Cisplatin, Carboplatin, Etoposide, Interferons, Procarbazine.

In addition, various sub-types of brain cancer tissues can be screened for their susceptibility to various anti-cancer therapies, by monitoring any change in the characteristic pattern of expressed genes selected from Table I, as compared with non-malignant cell expression.

Using the present invention, not only can drug candidates can be screened for potential efficacy using standardized malignant cell cultures, biopsy cells may be cultured and used to screen for efficacy as well. While it would be useful to have long term stable cultures of biopsy cells, the assays of the invention can be performed over a short period of time, thus avoiding the necessity of long term cultures. Thus, the assay of the invention can be performed on specific brain cancer tissue from individual patients, and the potential efficacy of various therapeutics may be tested on those specific cells.

Even if the biopsy sample is not robust enough, or large enough for direct assays of the invention, analysis of the biopsy sample for the characteristic expression of signals, will allow for the selection of a model cancer cell line, which expresses a similar panel of characteristic signals as the biopsy sample. This selected model cell line, and results of therapeutics on the model cell line, may then be used to assess potential therapeutics and treatment.

Example 9

Antisense Inhibition of Gene Expression

The invention encompasses antisense therapeutics which can be used to alter gene expression or RNA translation in targeted cells. Antisense therapy can be accomplished using the identified characteristic nucleic acid insert sequences and genes containing the sequence, the entire gene identified as being characteristic, identified known genes, and suitable fragments of all of these nucleic acids. The design and use of antisense therapeutics is described in the art (see for example Eguchi et al., "Antisense RNA", *Ann. Rev. Biochem.*, 1991, 60:631–52). Even more useful than just the insert fragments, the complete nucleic acid seqence for a novel gene, such as CINN-1, and known genes, allows for the preparation of many more anti-sense nucleic acid therapeutics designed for inhibiting translation of the corresponding protein. All antisense nucleic acids can further incorporate modified backbone structures which give unique functionality to the nucleic acid for use as a therapeutic agent. (See for example Verma & Eckstein, (1998), *Ann. Rev. Biochem.*, 67:99–134).

For example, antisense nucleic acids, either RNA, DNA or PNAs (Protein nucleic acids) can be designed to be complementary for the nucleic acid sequences given as SEQ ID NO. 1–9, in their entirety, or a selected fragment thereof. In particular, fragments of from 10 to 15 nucleic acids can be designed using the nucleic acids described by SEQ ID NO. 1–9. Smaller fragments may also be designed, however selection for hybridization strength, and half-life duration in use will need to be made using standard criteria of analysis and established practice in the art.

While a preferred form of the invention has been shown in the drawings and described, since variations in the preferred form will be apparent to those skilled in the art, the invention should not be construed as limited to the specific form shown and described, but instead is as set forth in the claims.

We claim:

1. A method for ascertaining the propensity of a cell for malignant phenotype, said cell being isolated or in a biological sample, said method comprising assaying the cell or biological sample for a signal indicating the transcription of a nucleic acid transcript, said transcript corresponding to at least one nucleic acid sequence selected from the group consisting of CINN 1 (SEQ ID NO.: 8), OP11 C1-3 (SEQ ID NO.: 4), FAS OP17 (SEQ ID NO.: 7).

2. The method of claim 1, wherein said transcript is detected by RT-PCR using at least one amplification primer corresponding to at least one of OP11 C1-3 (SEQ ID NO.: 4), FAS OP17 (SEQ ID NO.: 7), CINN 1 (SEQ ID NO.: 8).

3. The method of claim 1, wherein said transcript is detected by nucleic acid hybridization using at least one nucleic acid probe corresponding to at least one of OP11 C1-3 (SEQ ID NO.: 4), FAS OP17 (SEQ ID NO.: 7), or CINN 1 (SEQ ID NO.: 8).

4. The method of claim 3, wherein said assay is in situ hybridization.

5. The method of claim 1, wherein said transcript is detected by RNase protection assay.

6. A method for ascertaining the suitability of an anti-neoplastic drug candidate for efficacy in treating a malignancy, wherein said method comprises combining said candidate drug with a cell having a cancer phenotype, said cell being isolated or in a biological sample, detecting in said cell or biological sample any change in the expression of at least one nucleic acid sequence corresponding to at least one of OP11 C1-3 (SEQ ID NO.: 4), FAS OP17 (SEQ ID NO: 7), or CINN 1 (SEQ ID NO.: 8).

7. A method as in claim 6, wherein said malignant biological sample is a biopsy sample from a patient to be treated.

8. A method as in claim 6, wherein said malignant biological sample is a cell line.

9. A method as in claim 6, wherein said malignant biological sample is a cell.

10. A method for ascertaining the propensity of a cell for malignant phenotype, said cell being isolated or in a biological sample, said method comprising assaying the cell or biological sample for a signal indicating the transcription of at least a first and a second nucleic acid transcript, said first transcript corresponding to at least one nucleic acid sequence selected from the group consisting of OP11 C1-3 (SEQ ID NO.: 4), FAS OP17 (SEQ ID NO.: 7), and CINN 1 (SEQ ID NO.: 8), said second transcript corresponding to at least one nucleic acid sequence selected from the group consisting of OP2 C2-6 (SEQ ID NO. 1), OP7 C3-1 (SEQ ID NO.: 2), OP9 A4-2 (SEQ ID NO.: 3), OP11 G2-10 (SEQ ID NO. 5), FAS OP13 (SEQ ID NO. 6), and CINN 2 (SEQ ID NO. 9).

11. The method of claim 10, wherein said signal is detected by RT-PCR, said first transcript being amplified using at least one amplification primer corresponding to OP11 C1-3 (SEQ ID NO.: 4), FAS OP17 (SEQ ID NO.: 7), or CINN 1 (SEQ ID NO.: 8) said second signal being amplified using at least one amplification primer corresponding to OP2 C2-6 (SEQ ID NO. 1), OP7 C3-1 (SEQ ID NO.: 2), OP9 A4-2 (SEQ ID NO.: 3), OP11 G2-10 (SEQ ID NO. 5), FAS OP13 (SEQ ID NO. 6), or CINN 2 (SEQ ID NO. 9).

12. The method of claim 10, wherein said first and second transcripts are detected by nucleic acid hybridization, said first transcript being detected using at least one nucleic acid probe corresponding to OP11 C1-3 (SEQ ID NO.: 4), FAS OP17 C1-D (SEQ ID NO.: 7), or CINN 1 (SEQ ID NO.: 8), said second transcript being detected using at least one nucleic acid probe corresponding to OP2 C2-6 (SEQ ID NO. 1), OP7 C3-1 (SEQ ID NO.: 2), OP9 A4-2 (SEQ ID NO.: 3), OP11 G2-10 (SEQ ID NO. 5), FAS OP13 (SEQ ID NO. 6), or CINN 2 (SEQ ID NO. 9).

13. The method of claim 12, wherein said assay is in situ hybridization.

14. The method of claim 10, wherein said transcript is detected by RNase protection assay.

15. A method for ascertaining the suitability of an antineoplastic drug candidate for efficacy in treating a malignancy, wherein said method comprises combining said candidate drug with a cell having a cancer phenotype, said cell being isolated or in a biological sample, detecting in said cell or biological sample any change in the expression of at least a first and a second nucleic acid transcript, sad first transcript corresponding to at least one nucleic acid sequence selected from the group consisting of OP11 C1-3 (SEQ ID NO.: 4), FAS OP17 (SEQ ID NO.: 7), and CINN 1 (SEQ ID NO.: 8), said second transcript corresponding to at least one nucleic acid sequence selected from the group consisting of OP2 C2-6 (SEQ ID NO. 1), OP7 C3-1 (SEQ ID NO.: 2), OP9 A4-2 (SEQ ID NO.: 3), OP11 G2-10 (SEQ ID NO. 5), FAS OP13 (SEQ ID NO. 6), and CINN 2 (SEQ ID NO. 9).

16. A method as in claim 15, wherein said malignant biological sample is a biopsy sample from a patient to be treated.

17. A method as in claim 15, wherein said malignant biological sample is a cell line.

18. A method as in claim 15, wherein said malignant biological sample is a cell.

* * * * *

SEQUENCE LISTING

<160> NUMBER OF SEQ ID NOS: 9

<210> SEQ ID NO 1
<211> LENGTH: 204
<212> TYPE: DNA
<213> ORGANISM: Homo sapiens

<400> SEQUENCE: 1

```
tgccgagctg gtgaagaaat cttgtgggta ttctggaaat ttgatacgga gagaacttgg      60
tgagctatga attactctca gtctcctttt tacagggttg ttgtgatccc tcttttccag     120
aaaattctgt ggaatgtttc tgtaggactt tgttctccac aagcttgaat taaagcagga     180
ttcagtttga aaaaaaaaaa gctt                                            204
```

<210> SEQ ID NO 2
<211> LENGTH: 249
<212> TYPE: DNA
<213> ORGANISM: Homo sapiens

<400> SEQUENCE: 2

```
gaaacgggtg tagaagttaa ggacatagaa ttggtcatgt cacaagcaaa tgtgtcgaga      60
gcaaaggcag tccgagccct gaagaacaac agtaatgata ttgtaaatgc gattatggaa     120
ttaacaatgt aaccatatgg aagcaacttt ttttggtgtc tcaaaggagt aactgcagct     180
tggtttgaaa tttgtactgt ttctatcata aataagtta tggcttcttg ttggaaaaaa     240
aaaaagctt                                                             249
```

<210> SEQ ID NO 3
<211> LENGTH: 296
<212> TYPE: DNA
<213> ORGANISM: Homo sapiens

<400> SEQUENCE: 3

```
gggtaacgcc cgagatgaaa cagaattcta tttgggcaag agatgcgctt atgtatataa      60
agcaaagaac aacacagtca ctcctggcgg caaaccaaac aaaaccagag tcatctgggg     120
aaaagtaact cgggcccatg gaaacagtgg catggttcgt gccaaattcc gaagcaatct     180
tcctgctaag gccattgggc acagaatccg agtgatgctg taccctcaa ggatttaaac     240
```

```
taacgaaaaa tcaataaata aatgtggatt tgtgctcttg taaaaaaaaa aagctt        296
```

<210> SEQ ID NO 4
<211> LENGTH: 263
<212> TYPE: DNA
<213> ORGANISM: Homo sapiens

<400> SEQUENCE: 4

```
caatcgccgt aatggtagga aactttttc tgatacctct ttctttgtac tatgaaactc     60
tcaatcttcc tgtgccacaa atgtcactta aaattaacta ttttctctca gtcgtaatgg   120
tctcctttct cctcttctcc ttctcaagtc atctattcca ttttgttcag cttctccttt   180
aatatgagat tacgttccta tttggggaaa ggagtgggga aagactgtca aattgtcctg   240
attttgcgaa aaaaaaaaag ctt                                           263
```

<210> SEQ ID NO 5
<211> LENGTH: 180
<212> TYPE: DNA
<213> ORGANISM: Homo sapiens

<400> SEQUENCE: 5

```
caatcgccgt cactggggtg gcagtgtcct gggtcctaag tctgtggctc gtatcgccaa    60
gctcgaaaag gcaaaggcta agaacttgc cactaaactg ggttaaatgt acactgttga   120
gttttctgta cataaaaata attgaaataa tacaaatttt ccttcaaaaa aaaaagctt   180
```

<210> SEQ ID NO 6
<211> LENGTH: 226
<212> TYPE: DNA
<213> ORGANISM: Homo sapiens

<400> SEQUENCE: 6

```
cagcacccac atacatccaa gcaaaaagga tctcactgcc attgatggct gagtctgaaa    60
taaaatctag aactgactca ggtgcccagg atgactgact cctcatttct gagatattgg   120
cagttgccat gaactcagaa ggcactcttt atattgtact tggaaatttt caaattgttt   180
agaaattact accatgccca actttgattt ggaaaaaaaa aagctt                  226
```

<210> SEQ ID NO 7
<211> LENGTH: 327
<212> TYPE: DNA
<213> ORGANISM: Homo sapiens

<400> SEQUENCE: 7

```
aagcttttt tttttcgggc agcctgtgaa ttttcaacct ccttttggc ttttacaaag     60
ttgtggcagg caactgcttt ggcaattttt acaccaagct gaagtagtta atcgaagtaa   120
caccatcagg aaagggacaa agagacagca cgagtctctg gatcgctgac actgagaaac   180
acacaacatt actcccatga ttttcctctc gagtagctag ctggttgctg agttcctcag   240
ccttctcaat attccactcc tccacagcct ggtctatcct cttttcaagg cctgacttct   300
caacttttt cctttaaca agcggtc                                         327
```

<210> SEQ ID NO 8
<211> LENGTH: 1549
<212> TYPE: DNA
<213> ORGANISM: Homo sapiens

<400> SEQUENCE: 8

```
gaattcgcgg ccgcgtcgac gcgggcactc aaaatcttgg taaggaaagt cccatttggg    60
```

-continued

```
caaaaatatg tcgctgacta cgcaggtaat aaggttaggc tcagaggtat ccatgggaac    120
cactaataaa agtactagaa tatgtttggg aaggaaatat tggaaacggg tgaaaactta    180
ctgagggaca catgcaatgg tactaaatca tcacatacag cactatcatt aaaatgtaat    240
tagattagtg gaggaaccca tctaccatat ttacaatccc atataatcat tacacaataa    300
tcacataatc atattaatgc tatggagtat gtatttatcc tcattttaca tgtgaagcgg    360
cggcagctgc ttgggcgcgg tgcggtggtg actgagctac gagcctggcg gcgggtgtgc    420
gccgagcccc ggcccggccc ggccctcgcg tgcctcccag gctccgcacc cctgatgctg    480
cgcgggtgct gagcccgctt cggccgggac gatggtgaag tatttcctgg ccagagcgt    540 gctccggagt tcctgggacc aagtgttcgc cgccttctgg cagcggtacc cgaatccta    600 tagcaaacat gtcttgacgg aagacatagt acaccgggag gtgacccctg acccggaact    660
gctgtcccgg cgactcctga ccaagaccaa caggatgcca cgctgggccg agcgactatt    720
tcctgccaat gttgctcact cggtgtacgt cctggaggac tctattgtgg acccacagaa    780
tcagaccatg actaccttca cctggaacat caacccgcc cggctgatgg tggtggagga    840
acgatgtgtt tactgtgtga actctgacaa cagtggctgg actgaaatcc gccgggaagc    900
ctgggtctcc tytakcttat ttggkgtctc cagagctgtc caggaatttg gtcttgcccg    960
gttcaaaagc aacgtgacca agactatgaa gggttttgaa tatatcttgg ctaagctgca   1020
aggcgaggcc ccttccaaaa cacttgttga gacagccaag gaagccaagg agaaggcaaa   1080
ggagacggca ctggcagcta cagagaaggc caaggacctc gccagcaagg cggccaccaa   1140
gaagcagcag cagcagcaac agtttgtgta gccagtctac caccaccaca gcacccagca   1200
cagctaggct tagcccctct gccctccctt cattgtactt tatcattaaa aatcaacttc   1260
cagccctgtt tgctgtttac gtggtgggtt gtggggatgc agtttggcat ttgcagtaca   1320
ccaagcacat gattcatgtt tgagccaggt ctgcttattc tcccattggg cagctgagga   1380
ccgaggcaca gaggtgcggt gacttgcccg gggcttcagg tagcctgcag gttaactggc   1440
ggtaagtgct agactgtaag cccgacaagg gcagggcttt tggttttgtt ctctgatgtg   1500
tctcagtatt tagcacataa tagacactca ataaatactt gttgaattc                1549
```

<210> SEQ ID NO 9
<211> LENGTH: 1604
<212> TYPE: DNA
<213> ORGANISM: Homo sapiens
<220> FEATURE:
<221> NAME/KEY: misc_feature
<222> LOCATION: location 1287...1287
<223> OTHER INFORMATION: n = a, t, c, g
<220> FEATURE:
<221> NAME/KEY: misc_feature
<222> LOCATION: location 1290...1290
<223> OTHER INFORMATION: n = a, t, c, g
<220> FEATURE:
<221> NAME/KEY: misc_feature
<222> LOCATION: location 1445...1445
<223> OTHER INFORMATION: n = a, t, c, g
<220> FEATURE:
<221> NAME/KEY: misc_feature
<222> LOCATION: location 1453...1453
<223> OTHER INFORMATION: n = a, t, c, g
<220> FEATURE:
<221> NAME/KEY: misc_feature
<222> LOCATION: location 1456...1456
<223> OTHER INFORMATION: n = a, t, c, g
<220> FEATURE:
<221> NAME/KEY: misc_feature
<222> LOCATION: location 1529...1529

-continued

```
<223> OTHER INFORMATION: n = a, t, c, g

<400> SEQUENCE: 9
gaattcgcgg ccgcgtcgac caaggaagag tcttcagatg atgaagataa agaaagtgaa      60
gaggagccac caaaaaagac agccaaaaga gaaaaaccta aacagaaagc tacttctaaa     120
agtaaaaaat ctgtgaaaag tgccaatgtt aagaaagcag atagcagcac caccaagaag     180
aatcaaaaca gttccaaaaa agaaagtgag tctgaggata gttcagatga tgaacccttta    240 attaaaaagt tgaagaaacc ccctacagat gaagagttaa aggaaacaat aaagaaatta     300
ctggccagtg ctaacttgga agaagtcaca atgaaacaga tttcgcaaaa aggtctatga     360
aaattatcct acttatgatt taactgaaag aaaagatttc ataaaaacaa ctgtaaaaga     420
gctaatttct tgagatagag gacagagaag atgactcgtt cccatagatt tgaagatctg     480
atttatacca ttataccagc aaagagaatg tatttccttt tctaaatcct tgttaagcaa     540
cgttagtaga acttactgct gacctttta tcttgagtgt tatgtgaatt tgagtttgct      600
gttttaaatt gcatttctat gccattttta gtttaaaatc ttgcatggca ttaattgttc     660
cttgctttta tagttgtatt ttgtacattt tggatttctt tatataaggt catagattct     720
tgagctgttg tggtttttag tgcacttaat attagcttgc ttaaggcata cttttaatca     780
agtagaacaa aaactattat caccaggatt tatacataca gagattgtag tatttagtat     840
atgaaatatt ttgaatacac atctctgtca gtgtgaaaat tcagcggcag tgtgtccatc     900
atattaaaaa tatacaagct acagttgtcc agatcactga attggaactt ttctcctgca     960
tgtgtatata tgtcaaattg tcagcatgac aaaagtgaca gatgttattt ttgtattttt    1020
aaaaaacaat tggttgtata taaagttttt ttatttcttt tgtgcagatc acttttttaaa   1080 ctcacatagg taggtatctt tatagttgta gactatggaa tgtcagtgtt cagccaaaca    1140
gtatgatgga acagtgaaag tcaattcagt gatggcaaca ctgaaggaac agttaccctg    1200
ctttgcctcg aaagtgtcat caatttgtaa atttagtatt aactctgtaa aagtgtctgt    1260
aggacgtttt atattatata aggcagnccn aaaatcaacc tatcaaagct tcaaaaactt    1320
tgggaaaggg tgggattaag ccaagcacat ttggcttaca gtaaatgaac tgatttttat    1380
taactgcttt tgcccatata aaatgctgat atttactgga aacctagcca gcttcacgat    1440
tatgnctaaa gtnccngatt ataatgccag aatataatgt gcaggcaatc gtggatgtct    1500
ctgacaaagt gtgtctcaaa aataatatnc ttttacatta aagaaattta atgtttctct    1560
ggaaaaaaaa aaaaaaaaaa aaaagtcgac gcggccgcga attc                     1604
```